US008212216B2

(12) United States Patent
Perkins et al.

(10) Patent No.: US 8,212,216 B2
(45) Date of Patent: Jul. 3, 2012

(54) IN-LINE PROCESS MEASUREMENT SYSTEMS AND METHODS

(75) Inventors: David L. Perkins, Irmo, SC (US); Robert P. Freese, Pittsboro, NC (US); John C. Blackburn, Charleston, SC (US); Jonathan H. James, Columbia, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 168 days.

(21) Appl. No.: 12/594,001

(22) PCT Filed: Mar. 27, 2008

(86) PCT No.: PCT/US2008/058450
§ 371 (c)(1),
(2), (4) Date: Sep. 30, 2009

(87) PCT Pub. No.: WO2008/121715
PCT Pub. Date: Oct. 9, 2008

(65) Prior Publication Data
US 2010/0073666 A1    Mar. 25, 2010

Related U.S. Application Data

(60) Provisional application No. 60/908,983, filed on Mar. 30, 2007.

(51) Int. Cl.
*G01J 5/02*    (2006.01)
(52) U.S. Cl. .................................. 250/341.8; 356/318
(58) Field of Classification Search ............... 250/341.8; 356/318
See application file for complete search history.

(56) References Cited

U.S. PATENT DOCUMENTS

| 3,632,435 A | 1/1972 | Eriksson et al. |
| 3,717,078 A | 2/1973 | Ogura |
| 3,761,724 A | 9/1973 | Dennis |
| 4,084,880 A | 4/1978 | Clow |
| 4,118,106 A | 10/1978 | Leith |
| 4,499,378 A | 2/1985 | Miyatake et al. |

(Continued)

FOREIGN PATENT DOCUMENTS

EP     0 600 334 A2    6/1996
(Continued)

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.

(Continued)

*Primary Examiner* — David Porta
*Assistant Examiner* — Hugh H Maupin
(74) *Attorney, Agent, or Firm* — Haynes and Boone, LLP

(57) ABSTRACT

A method of using multivariate optical computing in real-time to collect instantaneous data about a process stream includes installing an optical analysis system proximate a process line, the process line being configured to move a material past a window of the optical analysis system; illuminating a portion of the material with a light from the optical analysis system; directing the light carrying information about the portion through at least one multivariate optical element in the optical analysis system to produce an instantaneous measurement result about the portion; and continuously averaging the instantaneous measurement result over a period of time to determine an overall measurement signal of the material.

23 Claims, 12 Drawing Sheets

U.S. PATENT DOCUMENTS

| | | | |
|---|---|---|---|
| 4,595,832 A | 6/1986 | LaDelfe et al. | |
| 4,607,914 A | 8/1986 | Fienup | |
| 4,687,335 A | 8/1987 | Zupanick et al. | |
| 4,687,337 A | 8/1987 | Stewart et al. | |
| 4,704,536 A | 11/1987 | Sugiyama et al. | |
| 4,821,338 A | 4/1989 | Naruse et al. | |
| 4,891,574 A | 1/1990 | Nagaya et al. | |
| 4,917,958 A | 4/1990 | Akai et al. | |
| 4,934,782 A | 6/1990 | Soffer et al. | |
| 4,968,148 A | 11/1990 | Chow et al. | |
| 4,981,332 A | 1/1991 | Smith | |
| 5,005,946 A | 4/1991 | Brandstetter | |
| 5,029,245 A | 7/1991 | Keranen et al. | |
| 5,071,526 A | 12/1991 | Pletcher et al. | |
| 5,090,807 A | 2/1992 | Tai | |
| 5,103,340 A | 4/1992 | Dono et al. | |
| 5,137,364 A | 8/1992 | McCarthy | |
| 5,150,236 A | 9/1992 | Patel | |
| 5,194,921 A | 3/1993 | Tambo et al. | |
| 5,223,715 A | 6/1993 | Taylor | |
| 5,259,381 A | 11/1993 | Cheung et al. | |
| 5,289,289 A | 2/1994 | Nagasaki | |
| 5,321,539 A | 6/1994 | Hirabayashi et al. | |
| 5,406,082 A | 4/1995 | Pearson et al. | |
| 5,412,465 A | 5/1995 | Baylor et al. | |
| 5,424,545 A | 6/1995 | Block et al. | |
| 5,459,677 A | 10/1995 | Kowalski et al. | |
| 5,479,164 A | 12/1995 | Yorks et al. | |
| 5,504,332 A | 4/1996 | Richmond et al. | |
| 5,513,022 A | 4/1996 | Son et al. | |
| 5,555,128 A | 9/1996 | Khoury et al. | |
| 5,622,868 A | 4/1997 | Clarke et al. | |
| 5,641,962 A | 6/1997 | Perry et al. | |
| 5,710,655 A | 1/1998 | Rumbaugh et al. | |
| 5,717,605 A | 2/1998 | Komiya et al. | |
| 5,734,098 A | 3/1998 | Kraus et al. | |
| 5,737,076 A | 4/1998 | Glaus et al. | |
| 5,747,806 A | 5/1998 | Khalil et al. | |
| 5,750,994 A | 5/1998 | Schlager | |
| 5,760,399 A | 6/1998 | Trygstad | |
| 5,771,096 A | 6/1998 | Andersen | |
| 5,781,289 A | 7/1998 | Sabsabi et al. | |
| 5,799,231 A | 8/1998 | Gates et al. | |
| 5,828,492 A | 10/1998 | Moser et al. | |
| 5,831,742 A | 11/1998 | Watson et al. | |
| 5,905,571 A | 5/1999 | Butler et al. | |
| 5,939,717 A | 8/1999 | Mullins | |
| 5,941,821 A | 8/1999 | Chou | |
| 5,945,676 A | 8/1999 | Khalil et al. | |
| 5,946,088 A | 8/1999 | Aldridge | |
| 5,946,089 A * | 8/1999 | Duer | 356/318 |
| 5,991,048 A | 11/1999 | Karlson et al. | |
| 6,006,585 A | 12/1999 | Forster | |
| 6,040,914 A | 3/2000 | Bortz et al. | |
| 6,124,937 A | 9/2000 | Mittenzwey et al. | |
| 6,137,108 A | 10/2000 | DeThomas et al. | |
| 6,176,323 B1 | 1/2001 | Weirich et al. | |
| 6,198,531 B1 | 3/2001 | Myrick et al. | |
| 6,304,854 B1 | 10/2001 | Harris | |
| 6,317,648 B1 | 11/2001 | Sleep et al. | |
| 6,347,131 B1 | 2/2002 | Gusterson | |
| 6,350,389 B1 | 2/2002 | Fujishima et al. | |
| 6,420,708 B2 | 7/2002 | Wilks, Jr. et al. | |
| 6,430,513 B1 | 8/2002 | Wang et al. | |
| 6,437,326 B1 | 8/2002 | Yamate et al. | |
| 6,469,785 B1 | 10/2002 | Duveneck et al. | |
| 6,476,384 B1 | 11/2002 | Mullins et al. | |
| 6,490,035 B1 | 12/2002 | Folestad et al. | |
| 6,517,230 B1 | 2/2003 | Afnan et al. | |
| 6,522,945 B2 | 2/2003 | Sleep et al. | |
| 6,529,276 B1 | 3/2003 | Myrick | |
| 6,573,999 B1 | 6/2003 | Yang | |
| 6,600,560 B2 | 7/2003 | Mikkelsen et al. | |
| 6,630,663 B2 | 10/2003 | Murphy et al. | |
| 6,667,802 B2 | 12/2003 | Faus et al. | |
| 6,690,464 B1 | 2/2004 | Lewis et al. | |
| 6,697,195 B2 | 2/2004 | Weber et al. | |
| 6,707,043 B2 | 3/2004 | Coates et al. | |
| 6,711,503 B2 | 3/2004 | Haaland | |
| 6,737,654 B2 | 5/2004 | Ducourant | |
| 6,741,335 B2 | 5/2004 | Kinrot et al. | |
| 6,748,334 B1 * | 6/2004 | Perez et al. | 702/24 |
| 6,765,212 B2 | 7/2004 | Goetz et al. | |
| 6,771,369 B2 | 8/2004 | Rzasa et al. | |
| 6,776,517 B2 | 8/2004 | Afnan et al. | |
| 6,798,518 B2 | 9/2004 | Difoggio et al. | |
| 6,853,447 B2 | 2/2005 | Goetz | |
| 6,870,629 B1 | 3/2005 | Vogel et al. | |
| 6,952,267 B2 | 10/2005 | Rarac | |
| 6,980,285 B1 | 12/2005 | Hansen | |
| 6,982,431 B2 | 1/2006 | Modlin et al. | |
| 6,995,840 B2 | 2/2006 | Hagler | |
| 7,006,214 B2 | 2/2006 | Rzasa et al. | |
| 7,123,844 B2 * | 10/2006 | Myrick | 398/192 |
| 7,138,156 B1 | 11/2006 | Myrick et al. | |
| 7,145,145 B2 * | 12/2006 | Benson | 250/339.07 |
| 7,173,239 B2 | 2/2007 | DiFoggio | |
| 7,245,374 B2 | 7/2007 | Hendriks | |
| 7,271,883 B2 | 9/2007 | Newell et al. | |
| 7,348,493 B2 | 3/2008 | Osanai et al. | |
| 7,399,968 B2 | 7/2008 | Lewis et al. | |
| 7,405,825 B2 | 7/2008 | Schuurmans et al. | |
| 7,411,729 B2 | 8/2008 | Lyama et al. | |
| 7,569,354 B2 | 8/2009 | Okano et al. | |
| 7,623,233 B2 | 11/2009 | Freese et al. | |
| 7,652,767 B2 | 1/2010 | Harsh et al. | |
| 7,671,973 B2 | 3/2010 | Van Beek et al. | |
| 7,697,141 B2 | 4/2010 | Jones et al. | |
| 7,853,104 B2 | 12/2010 | Oota et al. | |
| 7,889,346 B2 | 2/2011 | Myrick et al. | |
| 7,911,605 B2 | 3/2011 | Myrick et al. | |
| 7,920,258 B2 | 4/2011 | Myrick et al. | |
| 7,993,276 B2 | 8/2011 | Nazarian et al. | |
| 2001/0034064 A1 | 10/2001 | Turner et al. | |
| 2002/0008215 A1 | 1/2002 | Evans | |
| 2002/0050567 A1 | 5/2002 | Boudet et al. | |
| 2002/0071118 A1 | 6/2002 | Shinbori et al. | |
| 2002/0108892 A1 | 8/2002 | Goetz et al. | |
| 2002/0109094 A1 | 8/2002 | Goetz et al. | |
| 2002/0154315 A1 | 10/2002 | Myrick | |
| 2002/0154345 A1 | 10/2002 | Ozaki | |
| 2003/0056581 A1 | 3/2003 | Turner et al. | |
| 2003/0059820 A1 | 3/2003 | Vo-Dinh | |
| 2003/0071988 A1 | 4/2003 | Smith et al. | |
| 2003/0094495 A1 | 5/2003 | Knowles et al. | |
| 2003/0111606 A1 | 6/2003 | Berghmans et al. | |
| 2003/0117628 A1 | 6/2003 | Harju et al. | |
| 2003/0202179 A1 | 10/2003 | Larsen et al. | |
| 2004/0012782 A1 | 1/2004 | Mason et al. | |
| 2004/0106098 A1 | 6/2004 | Chen et al. | |
| 2004/0160601 A1 | 8/2004 | Womble et al. | |
| 2004/0197850 A1 | 10/2004 | Baer et al. | |
| 2004/0227086 A1 | 11/2004 | Haug et al. | |
| 2005/0077476 A1 | 4/2005 | Poteet et al. | |
| 2005/0087132 A1 | 4/2005 | Dickey et al. | |
| 2005/0167264 A1 | 8/2005 | Sternbergh et al. | |
| 2005/0251289 A1 | 11/2005 | Bonney et al. | |
| 2005/0264815 A1 | 12/2005 | Wechsler et al. | |
| 2005/0288906 A1 | 12/2005 | Drennen, III et al. | |
| 2006/0035018 A1 | 2/2006 | Sakurai et al. | |
| 2006/0051036 A1 | 3/2006 | Treado et al. | |
| 2006/0084879 A1 * | 4/2006 | Nazarian et al. | 600/500 |
| 2006/0093523 A1 | 5/2006 | Norman | |
| 2006/0142955 A1 * | 6/2006 | Jones et al. | 702/32 |
| 2006/0153492 A1 | 7/2006 | Treves et al. | |
| 2006/0158734 A1 | 7/2006 | Schuurmans et al. | |
| 2006/0169902 A1 | 8/2006 | Watanabe | |
| 2006/0197015 A1 | 9/2006 | Sterling et al. | |
| 2006/0276697 A1 | 12/2006 | Demuth et al. | |
| 2007/0035737 A1 | 2/2007 | Andrews et al. | |
| 2007/0137292 A1 | 6/2007 | Xian et al. | |
| 2007/0201136 A1 | 8/2007 | Myrick | |
| 2007/0282647 A1 | 12/2007 | Freese et al. | |
| 2007/0294094 A1 | 12/2007 | Alessandrini et al. | |
| 2008/0111064 A1 | 5/2008 | Andrews et al. | |
| 2008/0231849 A1 | 9/2008 | Myrick | |
| 2008/0276687 A1 | 11/2008 | Myrick et al. | |

| | | |
|---|---|---|
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick |
| 2009/0073433 A1 | 3/2009 | Myrick et al. |
| 2009/0097024 A1 | 4/2009 | Blackburn et al. |
| 2009/0140144 A1 | 6/2009 | Myrick et al. |
| 2009/0216504 A1 | 8/2009 | Priore et al. |
| 2009/0219538 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0042348 A1* | 2/2010 | Bakker ........................ 702/85 |
| 2010/0073666 A1 | 3/2010 | Perkins et al. |
| 2010/0141952 A1 | 6/2010 | Myrick et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0211329 A1 | 8/2010 | Farquharson et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0305741 A1 | 12/2010 | Myrick |
| 2010/0328669 A1 | 12/2010 | Myrick et al. |

FOREIGN PATENT DOCUMENTS

| | | | |
|---|---|---|---|
| EP | 1969326 A1 | 9/2008 | |
| EP | 1974201 A1 | 10/2008 | |
| EP | 2087328 A2 | 8/2009 | |
| EP | 2140238 A1 | 1/2010 | |
| JP | 57142546 A | 9/1982 | |
| JP | 4001558 A | 1/1992 | |
| JP | 07-053582 | 6/1996 | |
| JP | 11506206 | 6/1996 | |
| JP | 9-3662 | 1/1997 | |
| JP | 11506207 | 6/1999 | |
| WO | 96/30746 | 10/1996 | |
| WO | 2004/057284 A1 | 7/2004 | |
| WO | 2005/062006 A1 | 7/2005 | |
| WO | 2005/062986 A2 | 7/2005 | |
| WO | 2006/031733 A2 | 3/2006 | |
| WO | 2006/064446 A1 | 6/2006 | |
| WO | 2006/137902 A2 | 12/2006 | |
| WO | 2007/061435 A1 | 5/2007 | |
| WO | 2007/061436 A1 | 5/2007 | |
| WO | 2007/061437 A1 | 5/2007 | |
| WO | 2007/062202 A1 | 5/2007 | |
| WO | 2007/062224 A1 | 5/2007 | |
| WO | 2007/064578 A2 | 6/2007 | |
| WO | 2008/002903 A2 | 1/2008 | |
| WO | 2008/057912 A2 | 5/2008 | |
| WO | 2008/057913 A2 | 5/2008 | |
| WO | 2008/121684 A1 | 10/2008 | |

OTHER PUBLICATIONS

E.B. Martin et al., "Process Performance Monitoring Using Multivariate Statistical Process Control", IEE Proc.—Control Theory Appl., vol. 143, No. 2, pp. 132-144, Mar. 1996.

Mandelis et al., "Theory of Photopyroelectric Spectroscopy of Solids", Journal of Applied Physics, vol. 57, No. 9, pp. 4421-4430, 1985.

Zagonel et al., "Multivariate Monitoring of Soybean Oil Ethanolysis by FTIR", Talanta, vol. 63, No. 4, pp. 1021-1025, 2004.

Inon et al., " Combination of Mid- and Near-Infrared Spectroscopy for the Determination of the Quality Properties of Beers", Analytica Chimica Acta, vol. 571, No. 2, pp. 167-174, 2006.

Czarnik-Matusewicz et al., "Temperature-Dependent Water Structural Transitions Examined by Near-IR and Mid-IR Spectra Analyzed by Multivariate Curve Resolution and Two-Dimensional Correlation Spectroscopy", Analytica Chimica Acta, vol. 544, No. 1-2, pp. 15-25, 2005.

Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.

Ghesti et al., "Application of Raman Spectroscopy to Monitor and Quantify Ethyl Esters in Soybean Oil Transesterification", Journal of the American Oil Chemists' Society, vol. 83, pp. 597-601, 2006.

Dereniak et al., Infrared Detectors and Systems, John Wiley & Sons: New York, Chapter 9, pp. 395- 438, 1996.

Prystay et al., "Thermophysical Measurements and Interfacial Adhesion Studies in Ultrathin Polymer Films Using Homodyne Photothermal Spectrometry", Applied Spectroscopy, vol. 47, No. 4, pp. 501-514, 1993.

Simcock et al, "Tuning D* with Modified Thermal Detectors", Applied Spectroscopy, vol. 60, No. 12, pp. 1469-1476, 2006.

Lang, "Ferroelectric Polymers and Ceramic-Polymer Composites", Key Engineering Materials, vol. 92-93, pp. 83-142, 1994.

Profeta et al., "Spectral Resolution in Multivariate Optical Computing", Spectrochimica Acta Part A: Molecular and Biomolecular Spectroscopy, vol. 67, pp. 483-502, 2007.

Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.

Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.

Knothe, "Analyzing Biodiesel: Standards and Other Methods", Journal of the American Oil Chemists Society, vol. 83, No. 10, pp. 823-833, 2006.

E.D. Palik, Handbook of Optical Constants of Solids I, Academic Press, San Diego, pp. 350-357, 1998.

M.L. Myrick, "Multivariate optical elements simplify spectroscopy", Laser Focus World 38, 91-94, 2002.

O. Soyemi et al., "Design and testing of a multivariate optical element: The first demonstration of multivariate optical computing for predictive spectroscopy", Anal. Chem. 73, No. 6, pp. 1069-1079, (2001).

M.L. Myrick et al., "A single-element all-optical approach to chemometric prediction", Vib. Spectrosc. 28, 73-81, 2002.

A.M.C. Prakash et al., "Optical regression: a method for improving quantitative precision of multivariate prediction with single channel spectrometers", Chemom. Intell. Lab. Syst. 46, 265-274, 1999.

R.A. Deverse et al., "Realization of the Hadamard multiplex advantage using a programmable optical mask in a dispersive flat-field near-infrared spectrometer", Appl. Spectrosc. 54, 1751-1758, 2000.

F.G. Haibach et al., "Precision in multivariate optical computing", Appl. Optics 43, 2130-2140, 2004.

M.L. Myrick et al., "Application of multivariate optical computing to simple near-infrared point measurements", Proceedings of the SPIE, Bellingham, VA, US, vol. 4574, pp. 208-215, 2002.

O.S. Heavens, Optical Properties of Thin Solid Films, Dover Publications, Inc., Mineola, USA, pp. 62-81, 242-249, 1991.

S. Betancourt et al., "Analyzing Hydrocarbons in the Borehole", Oilfield Review, pp. 54-61, Autumn 2003.

D. Eastwood et al., "Field applications of stand-off sensing using visible/NIR multivariate optical computing", Ground and Air Pollution Monitoring and Remediation, SPIE vol. 4199, pp. 105-114, 2001.

Haibach et al., "On-line Reoptimization of Filter Designs for Multivariate Optical Elements", Applied Optics, vol. 42, No. 10, pp. 1833-1838, Apr. 1, 2003.

Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.

M.P. Nelson et al., "Multivariate optical computation for predictive spectroscopy", SPIE Vo. 3261, pp. 232-243, 1998.

O. Soyemi et al., "A Simple Optical Computing Device For Chemical Analysis", Proceedings of SPIE Vo. 4284, pp. 17-28, 2001.

O. Soyemi et al., "Design of angle tolerant multivariate optical elements for chemical imaging", Applied Optics, vol. 41, No. 10, pp. 1936-1941, Apr. 1, 2002.

O. Soyemi et al., "Nonlinear Optimization Algorithm for Multivariate Optical Element Design", Applied Spectroscopy, vol. 56, No. 4, pp. 477-487, 2002.

O. Soyemi et al., "Novel Filter Design Algorithm for Multivariate Optical Computing", Advanced Environmental and Chemical Sensing Technology, Proceedings of SPIE Vo. 4205, pp. 288-299, 2001.

Strausz et al., "About the Colloidal Nature of Asphaltenes and the MW of Covalent Monomeric Units", American Chemical Society, Energy and Fuels 16, No. 4, pp. 809-822, 2002 (abstract).

N. Aske et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 1304-1312, 2001.

N. Aske et al., "Asphaltene Aggregation from Crude Oils and Models Systems Studied by High-Pressure NIR Spectroscopy", Energy and Fuels, American Chemical Society, 16, No. 5, pp. 1287-1295, 2002.

Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.

Y. Yan et al. "Fluorescence Fingerprint of Waters: Excitation-Emission Matrix Spectroscopy as a Tracking Tool", Applied Spectroscopy, vol. 54, No. 10, pp. 1539-1542, 2000.

M.P. Nelson et al., "Multivariate optical computation for predictive spectroscopy", Analytical Chemistry, vol. 70, No. 1, pp. 73-82, Jan. 1, 1998.

M.P. Nelson et al., "Fabrication and evaluation of a dimension-reduction fiberoptic system for chemical imaging applications", Review of Scientific Instruments, vol. 70, No. 6, pp. 2836-2843, Jun. 1999.

M.L. Myrick, "New approaches to implementing predictive spectroscopy", Proceedings of the SPIE Conference on Pattern Recognition, Chemometrics, and Imaging for Optical Environmental Monitoring, SPIE vol. 3854, pp. 98-102, Sep. 1999.

M. Groner et al., "Identification of Major Water-Soluble Fluorescent Components of Some Petrochemicals", Marine Pollution Bulletin, vol. 42, No. 10, pp. 935-941, 2001.

M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.

M.L. Myrick et al., "Spectral tolerance determination for multivariate optical element design", Fresenius J Anal Chem, 369:351-355, 2001.

R.J. Priore et al., "Miniature Stereo Spectral Imaging System for Multivariate Optical Computing", Applied Spectroscopy, vol. 58, No. 7, pp. 870-873, 2004.

M.L. Myrick et al., "Use of Molecular Symmetry to Describe Pauli Principle Effects on the Vibration-Rotation Spectroscopy of $CO_2(g)$", Journal of Chemical Education, vol. 81, No. 3, pp. 379-382, Mar. 2004.

M.N. Simcock et al., "Precision in imaging multivariate optical computing", Applied Optics, vol. 46., No. 7, pp. 1066-1080, Mar. 1, 2007.

Ozturk et al., "Filtering Characteristics of Hybrid Integrated Polymer and Compound Semiconductor Waveguides", In: Journal of Lightwave Technology, vol. 20, No. 8, pp. 1530-1536, Aug. 2002.

P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.

Mullins et al., "Gas-Oil Ratio of Live Crude Oils Determined by Near-Infrared Spectroscopy", Applied Spectroscopy, vol. 55, No. 2, pp. 197-201, 2001.

Dobrowolski, J.A., et al., "Refinement of Optical Multilayer Systems With Different Optimization Procedures," *Applied Optics*, vol. 29, No. 9, Jul. 1, 1990, pp. 2876-2893.

Sullivan, Brian T., et al., "Implementation of a Numerical Needle Method for Thin-Film Design," *Applied Optics*, vol. 35, No. 28, Oct. 1996, pp. 5484-5492.

The Chemistry of Ferric Chloride; Printmaking Today, vol. 4, No. 2, 1995; Cello Press Ltd., Oxon, UK, 2 pages.

MSDS Hyper Glossary is a website http://www.ilpi.com/msds/ref/index.html, Safety Emporium Laboratory and Safety Supplies, retrieved on Feb. 10, 2012, 4 pages.

Handbook of Polymer Coating for Electronic Chemistry and Applications, 2nd ed., 1990.

Ryabenko, A.G., et al., "An Algorithm for Constructing the Basis of Optimal Linear Combinations . . . ", Pattern Recognition and Image Analysis, vol. 3, No. 1, 1993, 12 pages.

Moravskii, A.P., "Spectrophotometrtc Determination of the Yield of the C60 and C70 Fullerenes in Electric Arc Synthesis under Helium", Journal of Analytical Chemistry, vol. 53, No. 12, 1998, 8 pages.

MSDS No. F1080, Material Safety Data Sheet, Mallinckrodt Baker, Inc., Feb. 18, 2003, 6 pages.

Vasil'Ev, G.K., et al., "Rotational and Vibrational Deactivation of Excited HF Molecules", Soy. Physics-JETP, vol. 41, No. 4, 1976, pp. 617-621.

Ryabenko, A.G., et al., "Numerical Study of a Pattern Recognition Multispectral System With Optimal Spectral Splitting," Pattern Recognition and Image Analysis, vol. 1, No. 3, 1991, 10 pages.

\* cited by examiner

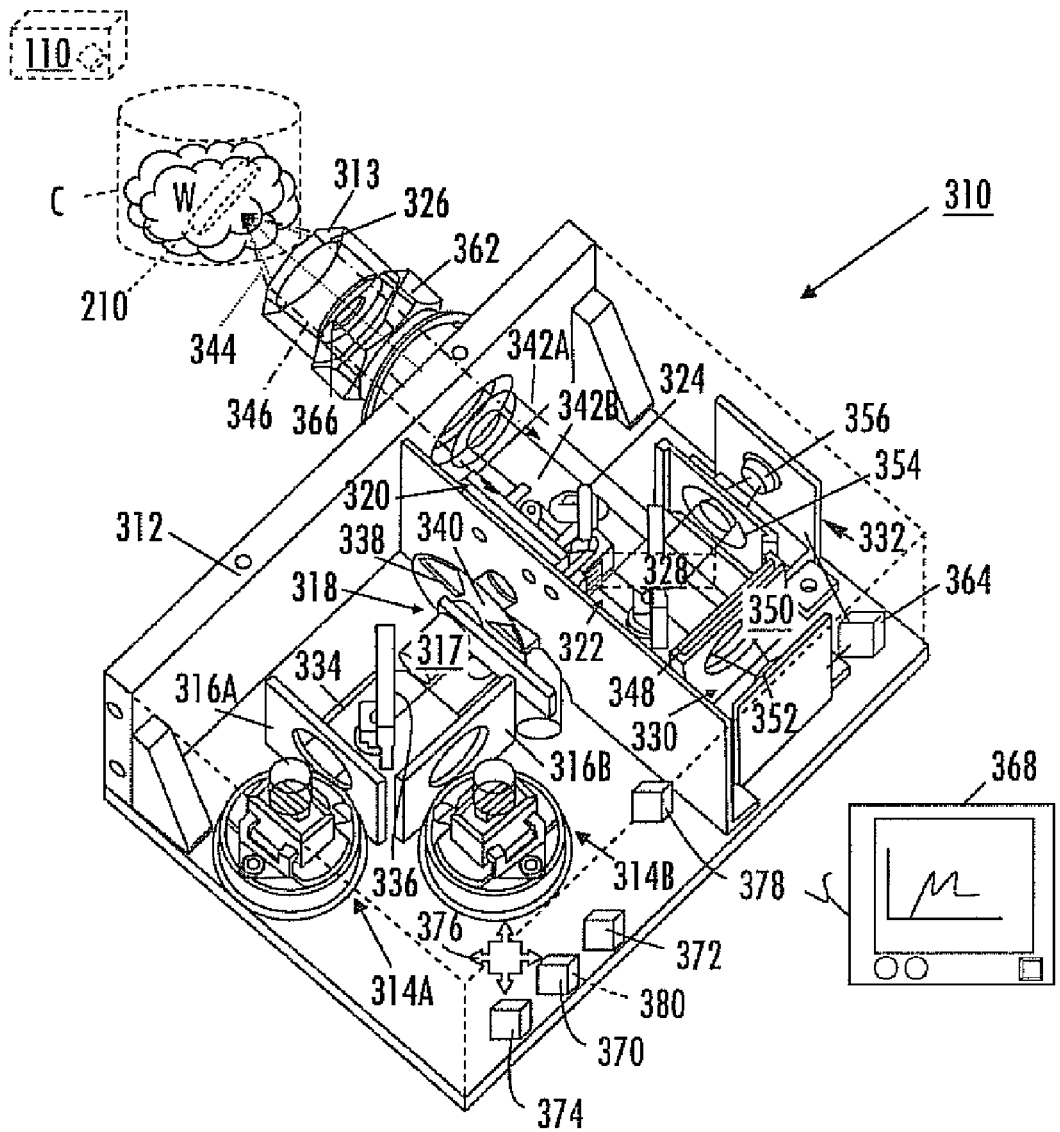
FIG. 7A
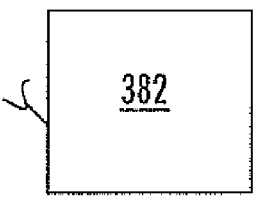

ns and Methods

CROSS-REFERENCE TO RELATED APPLICATIONS

This application is a non-provisional application that entered the national stage under 35 U.S.C. §371 from International Application Serial No. PCT/US08/058450, filed Mar. 27, 2008, which claims priority to U.S. Provisional Application Serial No. 60/908,983, filed Mar. 30, 2007, both of these applications now being expired. Applicants hereby claim priority to both of the above-referenced applications, the disclosures of which are incorporated by reference herein.

TECHNICAL FIELD

Provided herein are in-line process measurement systems and methods for achieving reliable, instantaneous measurements of various product parameters. The measurement system uses multivariate optical computing, using light to illuminate a portion of the target product and then directing the light through a multivariate optical element to a detector, to collect data instantaneously about the real-time product characteristics. The instantaneously collected data represents a mathematical relationship (e.g., a ratio) of signals produced by light that is reflected from the illuminated product. Such ratios are continuously averaged over time to provide a continuous measurement of product and/or process conditions of interest. In response to these continuous, real-time measurements, process conditions and/or equipment settings may be automatically modified, as necessary, to achieve the desired results.

BACKGROUND OF THE DISCLOSURE

Principles of Spectroscopic Analysis

Light conveys information through data. When light interacts with matter, for example, it carries away information about the physical and chemical properties of the matter. A property of the light—for example, its intensity—may be measured and interpreted to provide information about the matter with which it interacted. That is, the data carried by the light through its intensity may be measured to derive information about the matter. Similarly, in optical communications systems, light data is manipulated to convey information over an optical transmission medium (for example, a fiber optic cable). When the light signal is received, the data is measured to derive information.

In general, a simple measurement of light intensity is difficult to convert to useful information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive useful information from light. An estimate may be obtained, for example, by separating light from several samples into wavelength bands and performing a multiple linear regression of the intensity of these bands against the results of conventional measurements of the desired information for each sample.

For example, a polymer sample may be illuminated so that light from the polymer carries information such as the sample's ethylene content. Light from each of several samples may be directed through a series of band-pass filters that separate predetermined wavelength bands from the light. Light detectors following the band-pass filters measure the intensity of each light band. If the ethylene content of each polymer sample is measured using conventional means, a multiple linear regression of ten measured band-pass intensities against the measured ethylene content for each sample may produce an equation such as:

$$y = a_0 + a_1 w_1 + a_2 w_2 + \ldots + a_{10} w_{10} \quad \text{(``Equation 1'')}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate, since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the nth component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n Z_n.$$

The scalar multipliers $x_n$ may be considered the "magnitudes" of the principal components in a given light sample when the principal components are understood to have a standardized magnitude as provided by normalization.

Because the principal components are orthogonal, or perpendicular, they may be used in a relatively straightforward mathematical procedure to decompose a light sample into the component magnitudes, which accurately describe the data in the original sample. Given that the original light sample may also be considered a vector in the multi-dimensional wavelength space, the dot, or direct, product of the original signal vector with a principal component vector is the magnitude of the original signal in the direction of the normalized component vector. That is, it is the magnitude of the normalized principal component present in the original signal.

This is analogous to breaking a vector in a three dimensional Cartesian space into its X, Y, and Z components. The dot product of the threedimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal to each other, the dot product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example, differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94J, 1.07K, 1.13L, and 0.86M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \quad \text{("Equation 2")}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \quad \text{("Equation 3")}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a band-pass filter, a beam splitter, a lens, and a fiber optic cable. Light is reflected back through the cable and the beam splitter to another lens to a spectrograph. The spectrograph separates light from the illuminated sample by wavelength so that a detection device (such as a charge couple detector) can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property (for example, octane) and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability, and solid-state characteristics. Unfortunately, however, charge couple devices and their required operational instrumentation are very expensive. Furthermore, the devices are sensitive to environmental conditions. In a refinery, for example, they must be protected from explosion, vibration, and temperature fluctuations and are often placed in protective housings approximately the size of a refrigerator. The power requirements, cooling requirements, cost, complexity, and maintenance requirements of these systems have made them impractical in many applications.

Principles of Multivariate Optical Analysis

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer, which is highly selective to a particular analyte, may be constructed by designing simple calculations based on the filter transmission and reflection spectra. Other research groups have also performed optical computations through the use of weighted integration intervals and acousto-optical tunable filters, digital mirror arrays, and holographic gratings.

The measurement precision of digital regression has been compared to various optical computing techniques including MOEs, positive/negative interference filters, and weighted-integration scanning optical computing. In a high signal condition where the noise of the instrument is limited by photon counting, optical computing offers a higher measurement precision as compared to its digital regression counterpart. The enhancement in measurement precision for scanning instruments is related to the fraction of the total experiment time spent on the most important wavelengths. While the detector integrates or co-adds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

Multivariate optical computing (MOC), which is generally described in U.S. Pat. No. 6,198,531 B1 to Myrick et al. and in U.S. Pat. No. 6,529,276 B1 to Myrick, is used as a predictive spectroscopy technique that incorporates a multi-wavelength spectral weighting directly into analytical instrumentation. Both of these patents are incorporated herein for all purposes by reference thereto. Also incorporated by reference herein are the teachings of PCT Application No. PCT/US2007/083280, to Ometric Corporation, which describes a self-contained multivariate optical computing and analysis system.

Since multivariate optical element (MOE)-based MOC uses detectors that see all wavelengths emanating from an illumination source simultaneously—including wavelengths that carry no information—measurement noise is reduced and measurement precision is increased in these systems by making the system sensitive primarily to wavelengths carrying information. Additionally, a spectral range of the illumination source may be controlled by using band-pass filters or spectral elements having predetermined transmission characteristics. Further, in some embodiments, the system shines a light signal directly onto a sample, thus eliminating the use of, for instance, a fiber optic probe. Advantageously, the component parts of such an optical analysis system are simple and economical to manufacture, assemble, and use, with improved signal when the attenuation typical of a fiber optic probe is removed.

According to one embodiment taught in PCT/US2007/083280, an optical analysis system generally includes an illumination source for shining light or other radiative energy through a set of lenses. Light levels are maximized through the optical system to enhance transmission (reduce loss) of the light. The illumination source subsequently shines the light through a multi-window (e.g., 10-window) chopper wheel. The chopper wheel rotates, for instance, at 40 Hertz (Hz) to produce a light beam modulated at 400 Hz. A modulated light signal is beneficial for reliable performance of the photodetectors in the system.

The light beam then passes through one or more spectral elements or filters to control the spectral region of the light that passes through the elements or filter and, ultimately, onto a sample being analyzed. The light is reflected by a turning mirror down the center of the sampling tube and is focused by a lens on the sample. The sample reflects the light through the lens and back down the sampling tube, past the turning mirror. The light—which now carries data as a result of its interaction with the sample—passes through a beam splitter that reflects part of the light ("signal A") through a multivariate optical element (MOE) and lens and onto a photodetector. Another part of the light ("signal B"), which passes through a lens onto another photodetector, acts as a reference signal.

The system measures signal A and signal B, and a ratio of the two signals is generated to measure a concentration of the sample, e.g., a chemical of interest. Additionally, monitoring of signal A and/or signal B independently, or in some combination, may provide other information, such as powder segregation, packing of materials, and effect of particle size. More specifically, any algebraic combination of signals A and B may be used; e.g., A and/or B independently; A divided by B; A plus B; A minus B; B divided by A; B minus A, etcetera.

For example, a ratio of signal A to signal B may provide a chemical measurement, while, individually, the A signal and/or the B signal may provide other homogeneity measures, including physical make-up of the sample, packing, particle size, and/or separate physical and chemical properties.

According to another aspect of PCT/US2007/083280, which is applicable to the present disclosure, a method of determining information carried by light includes the steps of: (a) providing an optical analysis system having a multivariate optical element disposed to receive a source light from an illumination source; (b) filtering the source light through a spectral element in the optical element analysis system; (c) reflecting the filtered light through an inner region of a cavity in a first direction toward a sample to be measured, the cavity defining a second region disposed about the inner region; (d) focusing the reflected light proximate the sample; (e) reflecting the focused light from the sample through the second region in a second direction toward a beam splitter, the light being reflected from the sample carrying data from the sample; (f) splitting the sample data-carrying light with the beam splitter into a first light and a second light; (g) optically filtering the data of the first light with the multivariate optical element into an orthogonal component; (h) directing the first light filtered by the multivariate optical element onto a first photodetector; (i) directing the second light onto a second photodetector; and (j) comparing the orthogonal component of the first light to information present in the second light to determine a property of the sample. In this aspect, the light is focused on, in, or near the sample, the light having a focal point proximate the sample. Also in this aspect, the beam splitter is a 50/50 beam splitter.

The method may also include the step of modulating the light from about 50 Hz to about 5000 Hz before filtering the light through the spectral element. A further step may include controlling a spectral range of the light source, the spectral element having a predetermined transmission characteristic for controlling the spectral range. Also in this aspect, the spectral element may be two or more spectral elements for controlling the spectral range of the light source.

Further, the method may include measuring a concentration of the sample using a ratio of the first light and the second light. Additional steps may include monitoring the first light, the second light, or combinations thereof to assess particle segregation of the sample; to assess density of the sample; to assess the effect of particle size in the sample; to measure a chemical in the sample; to measure homogeneity of the sample; and combinations of the foregoing steps.

Although not preferred in the present system, the method may include the step of using a fiber optic probe. Moreover, the method may include preparing a chemometric model to make a similar measurement of the light reflected from the sample as a measurement made by the optical analysis system.

Another step may be comparing the illumination light from the outer annular region with the filtered light through the inner region of the cavity to determine the property of the sample.

In yet another aspect, an optical analysis system may be configured in a transmission mode, rather than a reflectance mode as in the foregoing embodiments. In the transmission mode, light passes through a sample (e.g., a fluid sample) and is collected on a far side of the sample to enable, for instance, study of particle density in the fluid sample in conjunction with chemical content. More particularly, the optical analysis system may be configured to operate in the transmission mode, in which the light is shone through the sample to a similar detection system. Additionally, or alternatively, a mirrored surface can be placed within the transmissive sample to reflect the light back into the detection system as described above.

PCT/US2007/083280 also provides a method of determining information carried by light that includes the steps of (a) determining a plurality of orthogonal components of a first portion of a light signal, wherein each of the components has a predetermined shape with respect to a property of the first portion of the light signal that varies over a predetermined wavelength range; (b) determining respective weightings for the orthogonal components so that the magnitude of the orthogonal components in the first portion of the light signal, weighted by the weightings, is proportional to the information present in the first portion in a predetermined relationship; (c) providing an optical filter mechanism configured to optically filter the orthogonal components; (d) disposing the optical filter mechanism to receive the first portion of the light signal; (e) disposing a detector to receive a second portion of the light signal; (f) detecting the property of the first portion of the light signal filtered by the optical filter mechanism; and (g) analyzing the sample in real time by comparing the property of the first portion of the light signal to information in the second portion of the light signal.

Further, the optical analysis system includes a light source being configured to radiate a first light along a first ray path; a modulator disposed in the first ray path, the modulator being configured to modulate the first light to a desired frequency; a spectral element disposed proximate the modulator, the spectral element being configured to filter the first light for a spectral range of interest for a sample; a cavity in communication with the spectral element, the cavity being configured to direct the first light in a direction toward the sample, the sample reflecting the first light as a second light, the cavity being further configured to direct the second light; a beam splitter being configured to split the second light into a first beam and a second beam; an optical filter mechanism disposed to receive the first beam, the optical filter mechanism being configured to optically filter data carried by the first beam into at least one orthogonal component of the first beam; a first detector mechanism in communication with the optical filter mechanism to measure a property of the orthogonal component; and a second detector mechanism being configured to receive the second beam for comparison of the property of the orthogonal component of the first beam with the second beam.

In this aspect, the cavity includes a first region and a second region, the first region being configured to direct the second light in a direction toward the beam splitter, the second region being configured to direct the first light in a direction toward the sample. This functionality is readily accomplished by means of a concentric tube, in which the inner annular region directs light toward the sample and the outer annular region directs light reflected from the sample to the beam splitter. Preferably, the concentric tube includes a mirror disposed therein, the mirror being used to direct the first light in the cavity in the direction of the sample.

Further in this aspect of the disclosure, the optical analysis system can include a gain mechanism in communication with at least one of the optical filter mechanism, the first detector mechanism and the second detector mechanism, the gain mechanism being configured to weight a magnitude of the property of the light orthogonal component.

The optical analysis system may additionally include a conical mirror that is configured to convert the first light reflecting from the sample into a second light. The conical mirror may include a coating of one of gold, aluminum, or other element or material, which is selected based on desired spectral region.

The optical analysis system may additionally include an accelerometer that is configured to control the data acquisition such that only detector signals received during the period of time when the system is in the proper orientation such that the material sample (e.g., aspirin) is in proximity to the interrogation window are used for calculation; a computer that has a data acquisition and conversion card, the computer disposed in the system in communication with the first and second detector mechanisms for signal processing; and a battery and charging system disposed in the system in electrical communication with the system to provide stand-alone operation capability.

As is readily apparent, the multivariate optical analysis systems described herein represent a significant advantage in real-time monitoring over traditional spectroscopy methods.

SUMMARY

The present disclosure provides a further advancement of prior multivariate optical analysis systems, such advancement resulting in an improvement in signal-to-noise ratio of the measurement results and in the generation of a calibration result for the material. These advancements lead to greater accuracy and precision in material analysis.

As provided herein, a method of using multivariate optical computing in real-time to collect instantaneous data about a process stream includes (a) installing an optical analysis system proximate a process line, the process line being configured to move a target material past a window of the optical analysis system; (b) illuminating a portion of the target material with a light from the optical analysis system; (c) directing the light reflected from the illuminated portion (that carries information about the portion) through at least one multivariate optical element in the optical analysis system to produce an instantaneous measurement result; and (d) continuously averaging the instantaneous measurement result over a period of time to determine an overall measurement signal of the material.

In this method, the optical analysis system may be installed at the process line using a Swagelok®-type fitting or other sanitary fitting. The process line may include a mixing vat, a reactor, or a conveyor. The conveyor may be a transport conveyor, a screw-drive conveyor, a paddle conveyor, or the like.

The material may be heterogeneous in shape, size, or color. More particularly, the material may be colored such as orange, red, green, and/or brown. Any two portions of the material may have a void between them, which the system accounts for in the overall calculation and measurement.

The light may be an infrared light, more particularly, NIR.

Additionally in this aspect, the instantaneous measurement result may be a reflectance measurement, a transflectance measurement, a transmission measurement or combinations thereof. Averaging the instantaneous measurement results over the period of time provides a rolling average of product properties, thereby improving the signal-to-noise ratio of the overall measurement signal. The period of time may be up to about 60 minutes.

Continuous, or rolling, averaging of the instantaneous measurement result over a predetermined period of time may also provide a calibration result for the material. The slope and offset of the calibration result may be adjusted for measuring different materials. Further, the calibration result permits measurement of an analyte of interest. The analyte of interest may be a nutrient, a moisture content, a fat content, a protein content, a carbohydrate content, a pharmaceutical characteristic, an alcohol content, a cholesterol content, and the like, and combinations thereof. For instance, the moisture content may be in a food product. The food product may be pet food, sugar, potatoes, pasta, and the like.

The method may also include clearing the window by moving the material from the window. For instance, a cleaning system may be disposed proximate the window for clearing the window, and/or the cleaning system may include a wiper system. Additionally, or alternatively, the system may include an air purge system.

Other features and aspects of the disclosure are discussed in greater detail below.

BRIEF DESCRIPTION OF THE DRAWINGS

A full and enabling disclosure of the present disclosure, including the best mode thereof known to one skilled in the art, is set forth more particularly in the remainder of the specification, including reference to the accompanying figures, in which:

FIG. 7A is top perspective view of a wireless unit in accordance with a further aspect of the present disclosure;

DETAILED DESCRIPTION OF THE DISCLOSURE

Figure 1:
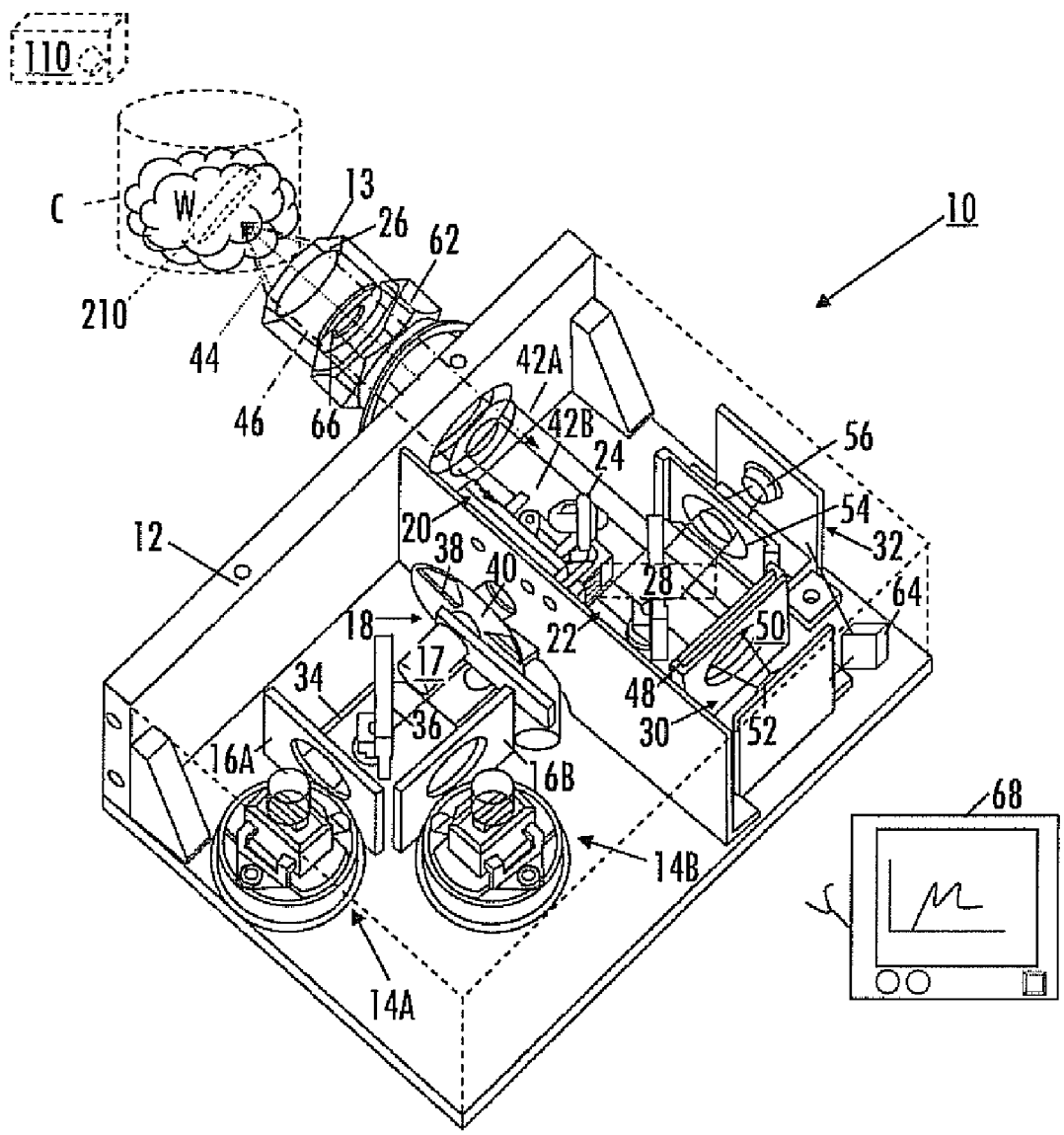
FIG. 1 is a top perspective view of one embodiment of a real time optical analysis, or measurement, system according to an aspect of the present disclosure.

Detailed reference will now be made to the drawings in which examples embodying the present inventions are shown. The detailed description uses numerical and letter designations to refer to features of the drawings. Like or similar designations of the drawings and description have been used to refer to like or similar parts of the disclosure.

The drawings and detailed description provide a full and written description of the examples in the disclosure, the manner and process of making and using those examples, and the best mode of carrying out the examples, so as to enable one skilled in the pertinent art to make and use them. However, the examples set forth in the drawings and detailed description are provided by way of explanation only and are not meant as limitations of the disclosure. The present disclosure thus includes any modifications and variations of the following examples as fall within the scope of the appended claims and their equivalents.

As used herein, the term "light" is broadly used to mean any form of radiation or radiative energy including, for instance, visible light or light in the infrared region. "Light" is also referred to herein as a light signal, a light beam, a light ray and the like to mean any form of radiative energy in the electromagnetic spectrum. Similarly, the term "transmission" can mean transmission of radiative energy onto a surface of a sample; penetration, however slight, into a sample such as a particulate sample or opaque fluid sample; or passage through a sample such as a fluid sample.

Briefly, with reference to FIGS. 1 and 2, the optical analysis systems of the present disclosure operate in the following manner. Illumination sources 14A, 14B generate source light beams 34, which shines through respective lenses 16A, 16B that are located proximate to the illumination sources 14A, 14B. Source light 34 then travels past a beam splitter 36 and is focused through a chopper-focusing lens 17. Source light 34 passes through windows 38 in a chopper wheel 18, windows 38 being defined as transmissive areas between spokes 40.

After passing through chopper wheel 18, source light 34 becomes a modulated light beam (that is, a plurality of light pulses). The source light 34 passes through one or more spectral elements 20 and reflects off a turning mirror 24. Turning mirror 24 causes the reflected light 44 to be directed through the inner annular region 42A of concentric sampling tube 22. Reflected light 44 travels through a Swagelok®-type connector 62, having at its distal end a focusing lens 66, and to the end of tube 22, where reflected light 44 passes through focusing lens 26 and a transmissive interrogation window 13 in container C.

Container C holds workpiece, or sample material, or material of interest, W. Within container C, reflected light 44 interacts with material of interest W and is reflected back from material W through an outer annular region 42B of concentric sampling tube 22 as data-carrying, or carrier, light 46. Because reflected light 44 was modulated, carrier light 46 is also in the form of a modulated beam of light pulses, each of which carries data from its interaction with material W.

Returning to the optical analysis device 10, carrier light 46 reaches beam splitter 28, which divides the light. Some of the carrier light 46 is sent in the direction of a detector 30 with a multivariate optical element (MOE) 48, through lens 50, and onto photodetector 52. This portion of the light may be referred to as "Signal A." The other portion of the carrier light 46 is sent through lens 54 and onto photodetector 56 on a detector 32. This second portion of the light may be referred to as "Signal B," which acts as a reference signal.

The detectors 30, 32 communicate with a gain mechanism 64, which compares the light of "Signal A" with that of "Signal B" and relays this information as a mathematical relationship (e.g., a ratio) to system 68. System 68 continuously averages the instantaneous measurements (that is, the ratios of Signal A to Signal B) for analysis and monitoring to provide continuous, instantaneous reporting of real-time product and/or process conditions.

These and other features and aspects of the multivariate optical computing system will be described in further detail in the disclosure herein.

Figure 2:
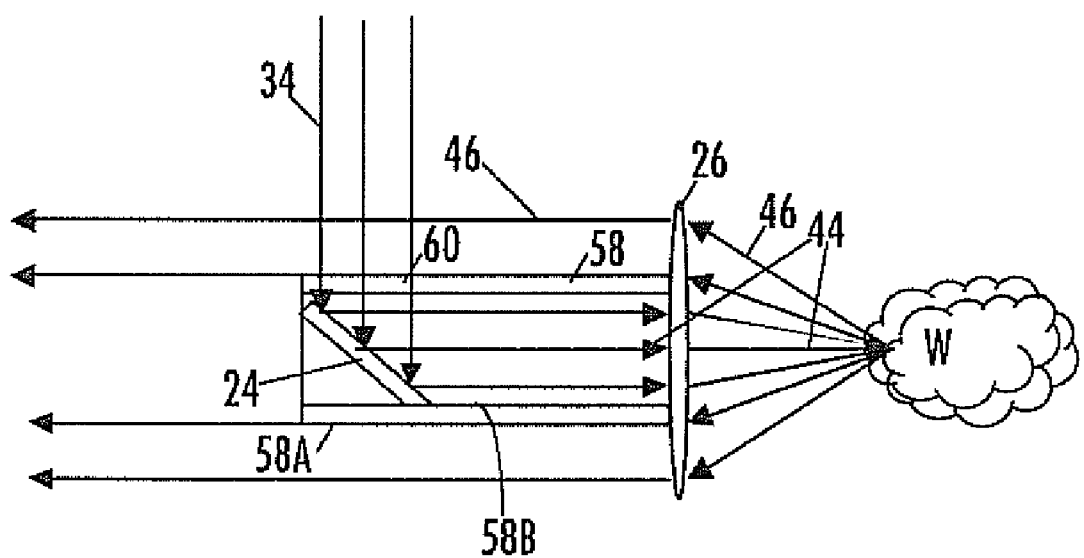
FIG. 2 is a schematic view of a concentric cavity as in FIG. 1 in accordance with a further aspect of the present disclosure.

As generally shown in FIGS. 1 and 2, an optical analysis system is designated by the element number 10. The system 10 is designed around at least one application-specific multivariate optical element (MOE) based on spectra typically provided by an end-user. System design takes into account representative spectra of compounds of interest and basic and expected concentrations of interest across a range of expected interferents. Also, the system 10 incorporates the desired spectral regions (UV, VIS, NIR, MIR, IR) of interest.

In the embodiment shown in FIG. 1, the optical analysis system 10 broadly includes a housing 12, a plurality of illumination or light sources 14A, 14B, a concentric light tube or cavity 22, a focusing lens 26, at least one beam splitter 28, a first detector 30 including a multivariate optical element 48, and a second detector 32. Although FIG. 1 shows a generally square- or rectangle-shaped, metallic housing 12 and two detectors 30, 32 arranged therein, the skilled artisan will instantly appreciate that a variety of shapes, dimensions, component placements, and material makeup of the components may be substituted for the examples shown, according to various requirements such as government regulations, customer specifications, and the like.

Moreover, as discussed below with respect to another embodiment of the disclosure, a workpiece or sample W can be analyzed using a Principal Component Regression (PCR)-type model without the beam splitter 28 in an off-line approach. As used herein, the workpiece or sample W refers to an analyte undergoing analysis over a range of conditions. The sample may be be a solid or a fluid, including, but not limited to, a powder, a pharmaceutical powder mixed with lactose and/or other excipient materials, a chemical, a polymer, a petroleum product, a solution, a dispersion, an emulsion, and combinations of these solids and fluids.

The skilled artisan will also understand that, although the system functions as a measurement system operating in reflectance mode, the system may also be configured to operate in a transmission mode, in which light is shone through the sample W from an incident side of the sample W to a similar detection system 110 on another side of the sample W. Alternatively, or additionally, a mirrored surface 210 may be placed within the transmissive sample to reflect the light back into the detection system 10. Therefore, the disclosure is not limited only to the examples shown in the figures.

With more particular reference to FIG. 1, the housing 12 (shown partially in phantom for clarity) may be made of metal (such as stainless steel); a plastic material, such as high-density polyethylene (HDPE); or any durable material for protecting the components of the optical analysis system 10. As shown, sampling of the sample W is accomplished through an interrogation window 13 installed in the wall of the container C. Accordingly, the enclosed optical analysis system 10 may be used in a dangerous (e.g., explosive) environment. As will be described in detail below, the interrogation window 13 is transmissive in a known manner in a spectral region of interest.

As briefly introduced above, the illumination sources 14A, 14B are chosen to provide a source light 34, which has a spectral range corresponding to a spectral range of interest for the intended sample measurement. The illumination sources 14A, 14B may also be chosen based on other factors, such as reliability, intensity, temperature generation, and other factors. The illumination sources 14A, 14B are redundant to further enhance reliability. As shown in FIG. 1, the redundant illumination sources 14A, 14B may be oriented at 90 degrees from each other with a "50-50" beam splitter 36 located near their center point to provide a constant source of illumination.

FIG. 1 further shows a pair of lenses 16A, 16B, respectively associated with the illumination sources 14A, 14B. The lenses 16A, 16B are used to collect the source light signal 34 from the illumination sources 14A, 14B and to focus the source light 34 on a modulator or chopper wheel 18, described below. As shown, the lenses 16A, 16B are positioned to capture as much of the source light 34 as possible from the illumination sources 14A, 14B. Additionally, a chopper-focusing lens 17 is used to focus as much of the source light signal 34 as possible through the chopper wheel 18.

The skilled artisan will instantly recognize the lenses 16A, 16B, 17 are selected for focal length, position, material of construction, and the like to enhance transmission (reduce loss) of the source light signal 34. For example, in the design of the optical path, if the illumination sources 14A, 14B are lamps, slight magnification or demagnification of the source is generally obtained at the sample W, depending on the ratios of the focal length, e.g., of the lens 16A to that placed after the illumination source 14A to collimate it.

Ultimately, the image of the illumination source 14A on the sample W is directed toward the detectors 30, 32 as described below and again with some slight magnification or demagnification, depending on the ratios of the focal length, e.g., of the lens 16A to that of, e.g., a lens 50 placed before the detector 30 to focus a reflected light 46 onto the detector 30. Thus, it should be understood that there is a relationship between the focal lengths of the lenses 16A, 16B that must be maintained in order to ensure that the ultimate image of the source-excited region of the sample W that is formed on the detectors 30, 32 is suited to the physical dimensions of the detectors 30, 32.

The lenses 16A, 168 shown for example in FIG. 1 are plastic, Fresnel lenses well suited for use in an infrared (IR) region of about 1000 nanometers (nm) to about 3000 nm. However, the skilled artisan will appreciate that the lenses 16A, 16B are not limited to only plastic, Fresnel lenses, but that other types of lenses and materials (such as glass) may be used for these lenses.

As further shown in FIG. 1, the chopper wheel 18 includes an alternating arrangement of windows 38 and spokes 40. The alternating windows 38 and spokes 40 modulate the source light signal 34 to a desired frequency in the range from about 50 Hertz (Hz) to about 5000 Hz. Such modulation enables a plurality of photodetectors 52, 56 in the optical system 10 to perform properly, as will be further described below.

As shown in this example, the chopper wheel 18 is a 10-window chopper wheel rotating at 40 Hz, which provides a chopped signal of 400 Hz.

The number and arrangement of the windows 38 and spokes 40 and, thus, the chopper frequency, are chosen based on several variables, including a rate of motion of the sample material W moving past the interrogation window 13; a performance characteristic of the photodetectors 52,56 and amplification system; a predetermined sampling rate of the data collection and analysis system 10; and physical properties of a chopper motor (not shown), control system (not shown), and the chopper wheel 18 (including material(s) of the windows 38).

More particularly, the number of windows 38 in the chopper wheel 18 may be adjusted to provide a suitable degree of signal modulation. In one aspect of the disclosure, the chopper wheel 18 has black spokes 40, which block the light signal 34, and open windows 38. In another aspect, different materials may be placed in the windows 38 to provide different spectral characteristics for the various windows 38. Moreover, the transmission characteristic of these windows 38 may be used as further spectral elements. The windows 38 may also contain multivariate optical elements (MOE), such as those described below with respect to a MOE 48 of the MOE detector 30.

FIG. 1 also shows a plurality of band-pass filters or spectral elements 20 located in a path of the source light signal 34 after the source light signal 34 has passed through the chopper wheel 18. As briefly discussed above, the spectral elements 20 are selected based on a desired application; i.e., to analyze a particular sample W. The spectral elements 20 are chosen so that the spectral region of illumination covers the desired range; that is, the selection of spectral elements 20 is related to a particular chemical material of interest. For example, if the desired spectral region encompasses light having wavelengths of 1500-2000 nanometers (nm), the spectral elements 20 are selected to filter out wavelengths are not in that region. An example of these spectral elements is a SCHOTT brand filter, which may be a long pass, short pass, or band-pass filter. By way of further example, but not of limitation, some suitable materials for use as the spectral elements 20 are listed in TABLE 1.

TABLE 1

Properties of Select Transmitting Materials

| Material (Comments) | SWL[1,3] (cm$^{-1}$) | LWL[2,3] (cm$^{-1}$) | RI[4] | Solubility (g/100 g) | Hardness (Kg/mm$^2$) | MP[5] (° C.) | pH Range |
|---|---|---|---|---|---|---|---|
| AMTIR (SeAsGe glass) | 11000 | 593 | 2.5 | 0 | 170 | 370 | 1-9 |
| BaF$_2$ (Barium Fluoride) | 66600 | 691 | 1.45 | 0.17 | 82 | 1280 | 5-8 |
| CaF$_2$ (Calcium Fluoride) | 79500 | 896 | 1.4 | 0.0017 | 158 | 1360 | 5-8 |
| CsI (Cesium Iodide; very hygroscopic) | 42000 | 172 | 1.73 | 44 | 20 | 621 | NA |
| Diamond (Type IIa; strong IR absorbance between 2700 and 2800 cm$^{-1}$) | 30000 | <2 | 2.4 | 0 | 5700 | 550 fp | 1-14 |

TABLE 1-continued

Properties of Select Transmitting Materials

| Material (Comments) | SWL[1,3] (cm$^{-1}$) | LWL[2,3] (cm$^{-1}$) | RI[4] | Solubility (g/100 g) | Hardness (Kg/mm$^2$) | MP[5] (° C.) | pH Range |
|---|---|---|---|---|---|---|---|
| Ge (Germanium; becomes opaque at elevated temperatures) | 5500 | 432 | 4 | 0 | 780 | 936 | 1-14 |
| KBr (Potassium Bromide) | 48800 | 345 | 1.52 | 53 | 6 | 730 | NA |
| KCl (Potassium Chloride) | 55600 | 385 | 1.45 | 35 | 7 | 776 | NA |
| KRS-5 (Thallium Bromide/ Thallium Iodide) | 17900 | 204 | 2.37 | 0.05 | 40 | 414 | 5-8 |
| NaCl (Sodium Chloride) | 52600 | 457 | 1.49 | 36 | 18 | 801 | NA |
| Polyethylene (For Far-IR, swells with some organic solvents) | 625 | <4 | 1.52 | 0 |  | 110 | 1.5-14 |
| SiO$_2$ (Silicon Dioxide) | 50000 | 2315 | 1.53 | 0 | 460 | 1713 | 1-14 |
| Si (Silicon; strong absorbance between 624 and 590 cm$^{-1}$) | 8900 | 624,30 | 3.41 | 0 | 1150 | 1420 | 1-12 |
| ZnS (Zinc Sulfide) | 17000 | 690 | 2.2 | 0 | 240 | 1830 | 5-9 |
| ZnSe (Zinc Selenide) | 15000 | 461 | 2.4 | 0 | 120 | 1526 | 5-9 |

[1]SWL = shortest wavelength for transmission, 1 mm, 50% transmission
[2]LWL = longest wavelength for transmission, 1 mm, 50% transmission
[3]To convert from wave number (cm$^{-1}$) to wavelength (μm), divide 10,000 by the wavenumber. For example, 5500 cm−1 is equivalent to 1.8 μm or 1800 nm.
[4]RI = Refractive Index at relevant wavelength
[5]MP = Melting Point With reference now to FIGS. 1 and 2, the light signal 34 exits the spectral elements 20 and reflects off a first mirror or turning mirror 24. Although the turning mirror 24 is shown at an angle of about 45 degrees with the source light 34 reflecting at this angle, the turning mirror 24 may be turned to any desired angle. As known to those skilled in the art, the turning mirror 24 may be a powered turning mirror powered by a battery, by electricity or the like. Further description of power sources and implementation with the turning mirror 24 is not necessary for one skilled in the art to understand this aspect of the disclosure. In addition, although the turning mirror 24 is shown as a unitary mirror, multiple mirrors may be utilized and arranged in, or adjustable to, a variety of positions.

As further shown in FIGS. 1 and 2, the filtered and reflected source light 34 becomes a reflected light 44 after being reflected by the turning mirror 24. The reflected light 44 thus continues down the concentric sampling tube 22, briefly introduced above, in a direction of the sample W. As shown and further described below, the concentric tube 22 includes an inner annular region 42A and an outer annular region 42B. In this example, the reflected light 44 is reflected along the inner annular region 42A. The illumination sources 14A, 14B and the detectors 30, 32 are shown in an exemplary orientation and may be reversed. It will be further appreciated that the source light 34 and the reflected light 44 are shown collimated for simplicity. However, the source light 34 and the reflected light 44 may not be completely collimated because the illumination sources 14A, 14B may be extended rather than point sources.

The focusing lens 26 in FIGS. 1 and 2 is located near an end of the tube 22 proximate the sample W. As shown in this example, the end of the tube 22 is sealed by being placed in contact with the transmissive interrogation window 13, which is installed in container C. The interrogation window 13 is preferably uniformly transmissive across wavelengths, but if it is not, the transmission characteristics of the interrogation window 13 are taken into account for the design of the system 10 and in particular the MOE 48. This embodiment may include an additional focusing lens 66, which can be solid or have one or more apertures as shown in FIG. 1. The additional focusing lens 66 is used to focus or collimate a carrier light 46, described below, in a direction of the tube 22.

The focusing lens 26 focuses the reflected light 44 onto, into or near the sample W via the transmissive interrogation window 13. In this example, the reflected light 44 is focused with a focal point 0-5 mm into the sample W. In addition to isolating components of the optical analysis system 10 from an external environment, the transmissive window 13 further enables a mixing vessel or container C, which is being tested/ sampled into, to remain intact. As shown in this example, a one-inch (inner diameter) Swagelok® brand connector 62, available from Swagelok Corporation of Solon, Ohio, is used to connect the optical analysis system 10 to the mixing vessel C. This arrangement causes the reflected light 44 to travel through the tube 22 (inner region 42A), to interact with the material of interest W, to reflect back through the tube 22 (outer region 42B), and to be directed to the detectors 30, 32, as further described below.

As most clearly shown in FIG. 2, a tube 58 defines an aperture 60 for passage of the source light 34 in a direction of the turning mirror 24, where the source light 34 is deflected off the face of the turning mirror 24 as reflected light 44. The reflected light 44 passes through lens 26 and interacts with sample W. This interaction produce data-carrying carrier light 46, which bounces off sample W, and returns through lens 26. The reflected light 44 and the data-carrying carrier light 46 may be defined or separated by physically separating the inner and outer regions 42A, 42B employing the tube 58. Any minimal reduction in light return of the carrier light 46 (caused by physical occupation of a portion of the outer region 42B by the tube 58) is offset by improvement in the amount of backscattered radiation returned to the detectors 30, 32 without encountering the sample W.

More specifically, the tube 58 is used to reduce a non-zero background measurement. The non-zero background measurement can occur in an optical system when a small amount of scattered light is returned to a detector even when no sample is present. Some of the scattered light may be reflected from a window, and some may come from the lenses themselves.

FIG. 2 shows that the tube 58 is placed around the mirror 24 before the lens 26. The tube 58 reduces background signals by separating the source light 34 and carrier light 36 to minimize "cross-talk". As shown, the tube 58 includes an aperture 60 for passage of the source light 34 in a direction of the turning mirror 24. As further shown, a conical extension 58A of the tube 58 may be placed after the mirror 24 in a direction of the detector 30. A thickness of the tube 58 should be minimized.

Also shown in FIG. 2, the tube 58 may have specular interior and exterior surfaces as well as a highly reflective coating 58B, such as gold, applied by electrolysis deposition, evaporation or other thin film coating method. The coating 58B reflects rays 34, 44 that would ordinarily terminate at a surface of the tube 58 back into respective optical paths from which they came. An image of the illumination source 14A, 14B may be silhouetted, but the "lost" light in the image is still focused to a spot within the zone illuminated by the illumination source 14A, 14B. Likewise, the returning carrier light 46 outside the tube 58 can be kept from being lost by traveling inside an outer tube with a specular reflecting surface (not shown, but surrounding the outer light path). This will keep light loss to a minimum while keeping the input and output paths relatively isolated from one another.

As introduced above, the carrier light 46 shown in FIGS. 1 and 2 which has been reflected from the sample W, travels through the outer annular region 42A of the sampling tube 22, past the turning mirror 24. The carrier light 46 reaches the beam splitter 28 (one of its operating positions shown in phantom). The beam splitter 28 divides the carrier light 46 with a neutral or gray spectrum, sending some of the carrier light 46 in a direction of the first or Multivariate Optical Element (MOE) detector 30 through the MOE 48, briefly introduced above, and through a first lens 50 onto the photo-detector 52, also briefly introduced above. The beam splitter 28 sends some other portion of the carrier light 46 through a second lens 54 onto the other detector 56, also briefly introduced above.

As shown in TABLE 2, by way of example but not of limitation, some detectors suitable for use as the detectors 52, 56 include:

TABLE 2

| Detector | Wave Range ($\lambda\mu$) | Detectivity $D^6$ | Cut Off Frequency ($H_z$) | Operating Temperature (K) |
|---|---|---|---|---|
| Photo-Transistor Type | | | | |
| Pt—S | 0.35-0.6 | 30 | $10^8$ | 295.0 |
| Si p-n PD | 0.4-1.0 | 50 | $10^7$ | 295.0 |
| Si p-i-n PD | 0.4-1.1 | 80 | $10^8$ | 295.0 |
| Si APD | 0.4-0.8 | 80 | $10^{10}$ | 295.0 |
| Ge p-n PD | 0.6-1.8 | 50 | $10^7$ | 295.0 |
| InSb p-n PD | 3.0-6.2 | 8 | $5 \times 10^2$ | 77.0 |
| PbSnTe p-n PD | 5.0-11.4 | >15-60 V/W | 10 | 77.0 |
| Photo-Conductor Type | | | | |
| PbS | 0.5-3.8 | 15.00 | 300 | 196.0 |
| PbSe | 0.8-4.6 | 3.00 | $3 \times 10^3$ | 196.0 |
| PbTe | 0.8-5.5 | 0.16 | $3 \times 10^3$ | 196.0 |
| p-InSb | 2.0-6.7 | 2.00 | $2 \times 10^5$ | 77.0 |
| n-InSb | 1.0-3.6 | 30.00 | $2 \times 10^6$ | 195.0 |
| PbSnTe | 5.0-11.0 | 1.7 | $8 \times 10^5$ | 4.2 |
| CdHgTe | 5.0-16.0 | 3.00 | $10^4$ | 4.2 |
| Ge:Au | 2.0-9.5 | 0.02 | $10^4$ | 77.0 |
| Ge:Zn,Au | 5.0-40.0 | 1.00 | $10^3$ | 4.2 |
| Ge:Cu | 5.0-30.0 | 3.00 | $10^3$ | 4.2 |
| Si:Al | 2.0-16.0 | 1.00 | $10^4$ | 27.0 |
| Si:Sb | 2.0-31.5 | 1.80 | $10^4$ | 4.0 |
| Pyroelectric Type | | | | |
| ATGS | 1-1000 | 0.030 | 10 | 295.0 |
| $(Ba,Sr)TiO_3$ | 1-1000 | 0.011 | 400 | 295.0 |
| Miscellaneous Other | | | | |
| Si | 0.2-1.1 | — | — | — |
| Ge | 0.4-1.8 | — | — | — |
| InAs | 1.0-3.8 | — | — | — |
| InGaAs | 0.8-3.0 | — | — | — |
| InSb | 1.0-7.0 | — | — | — |
| InSb (77K) | 1.0-5.6 | — | — | — |
| HgCdTe (77K) | 1.0-25.0 | — | — | — |

$^6 10^{10} \, cmHz^{1/2} W^1$

As further shown in FIG. 1, a gain mechanism 64 communicates with the detectors 30, 32 and the MOE 48. The gain mechanism 64 weights a magnitude of the property of an orthogonal component of a portion of the carrier light 46 as described, for instance, in U.S. Pat. No. 6,198,531 B1 to Myrick et al. and in U.S. Pat. No. 6,529,276 B1 to Myrick.

The beam splitter 28 is not required in an alternative embodiment of the disclosure in which a signal from the sample W is analyzed using a Principal Component Regression (PCR)-type model in an off-line approach. This alternative embodiment and approach is useful, for instance, for studying signals independently. More particularly, a system substantially as described above but without the beam splitter 28 is used to take an integral of the light on a detector similar to the detector 30 described above. By analyzing frequency-dependent intensities, results similar to those of the foregoing embodiment are produced, although possibly with a relatively slower response time than the present embodiment.

Also, in an additional aspect of the disclosure as shown in FIG. 1, a system 68 using an electrochemical or chemometric model can be employed in conjunction with any of the foregoing embodiments to make similar or same measurements of the carrier light 46 reflected from the sample W as the measurements described in the foregoing embodiments. By way of example, but not of limitation, the system 68 may be one as described by Myrick et al. in PCT Publication Number WO 05/062986, and U.S. patent application Ser. No. 10/581, 407, both of which are based on U.S. Provisional Application No. 60/533,570, filed Dec. 31, 2003, which are incorporated herein by reference to these applications.

In addition to the reflectance mode described above, one or more optical analysis systems can operate in a transmission mode in conjunction with the foregoing embodiments. In such a case, light is directed (passes) through the sample W, e.g., a fluid sample, and is collected on an opposite side of the sample W to enable study of particle density in the fluid, in conjunction with the chemical content described above. For instance, the system 10 may be configured to operate in transmission mode where the light is shone through the sample W to a similar detection system 110, as shown in FIG. 1 (in phantom for clarity). Additionally, or alternatively, a mirrored surface 210 may be placed within the transmissive sample W to reflect the light back into the system 10.

Figure 3:
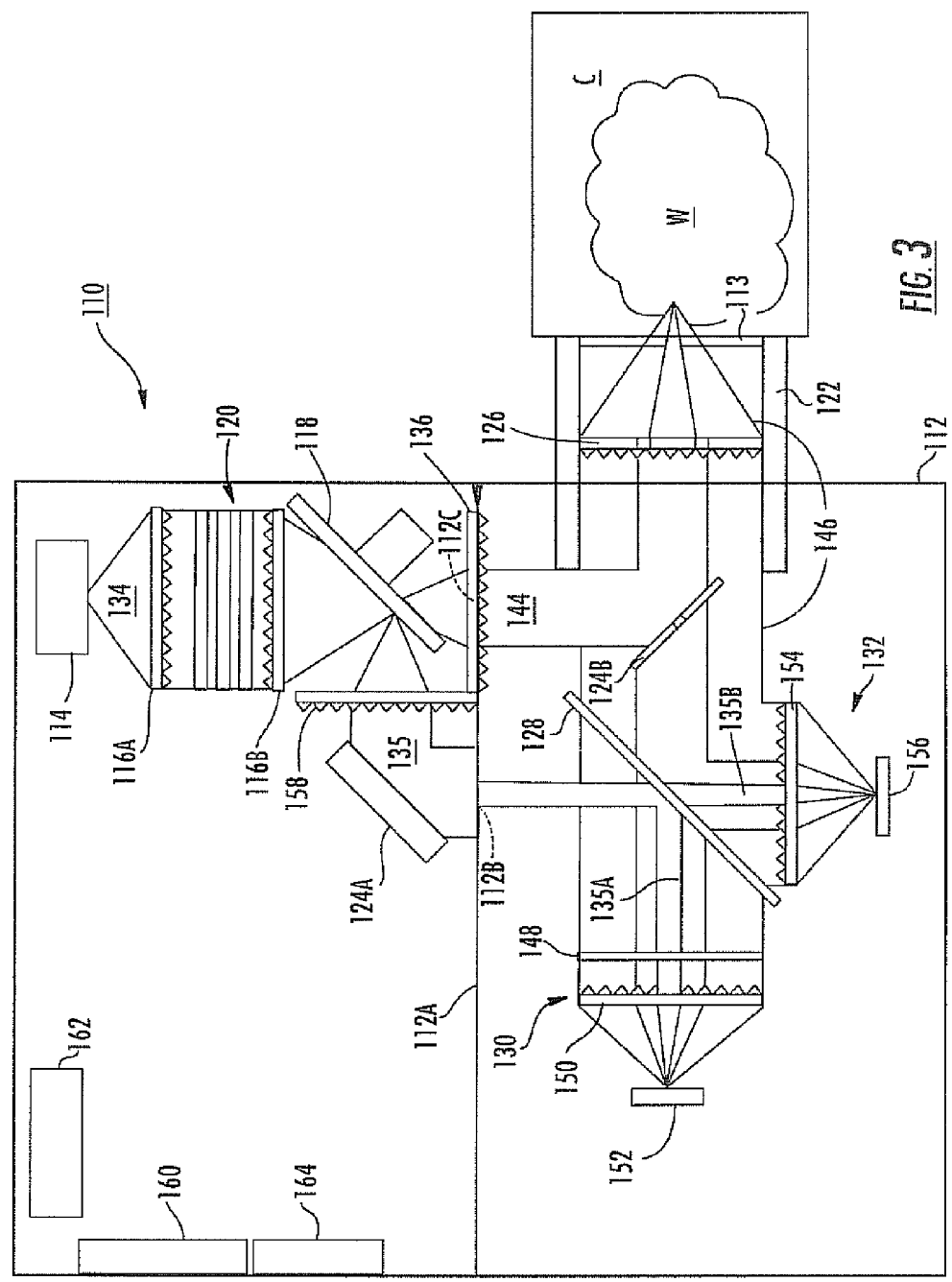
FIG. 3 is schematic plan view of another embodiment of a real time optical analysis, or measurement, system according to another aspect of the present disclosure.

With reference now to FIG. 3, a second exemplary embodiment of the present subject matter is designated generally by reference number 110. Many aspects of the optical analysis system 110 and related components are similar to the foregoing embodiment; thus, for the sake of brevity, only certain differences are described below. However, to provide a full and enabling disclosure of the optical analysis system 110, when like or similar elements and components are not specifically described below, implicit reference is made to the foregoing descriptions.

As shown in FIG. 3, the optical analysis system 110 broadly includes a housing 112, an illumination or light source 114, a chopper wheel 118, one or more spectral elements 120, a focusing lens 126, a beam splitter 128, a first detector 130 including a multivariate optical element 148, and a second detector 132. The optical analysis system 110 further includes an electrical connection 160, a pressurization sensor 162, and a purge gas assembly 164, which those skilled in the art will readily understand; therefore, further description is not necessary to understand and practice these aspects of the disclosure.

With more particular reference to FIG. 3, the illumination source 114 is rated for at least about 10,000 hours of operation, which alleviates a need for redundant illumination sources, though they may be provided if desired. The illumination source 114 provides a source light 134, which passes through a collecting Fresnel lens 116A. In this example, the collecting Fresnel lens 116A is sized to be about 1.5 square inches and is spaced about 0.6 inches from the illumination source 114. These dimensions may be adjusted according to particular system requirements and should not be interpreted as limitations of the disclosure.

As further shown in FIG. 3, the source light 134 passes into and through the spectral element(s) 120, which filter out undesired wavelengths to define a desired spectral region, e.g., 1500-2000 nm, in order to target a particular chemical material of interest. The source light 134 is focused by focusing Fresnel lens 116B, which is also sized to be about 1.5 square inches and spaced about 1 inch from the chopper wheel 118. As shown, the chopper wheel 118 reflects a portion of source light 134 as a calibration or reference light 135 and a transmitted light 144. Calibration light 135 is collimated by lens 158 before being reflected from a first mirror 124A through an adjustable aperture 112B in a bulkhead 112A of the housing 112. The aperture 112B is adjustable to dictate a desired amount of the calibration light 135. Finally, calibration light 135 impinges on beam splitter 128, thereby sending a portion 135A of calibration light 135 to the first MOE detector 130 and a portion 135B of calibration light 135 to the second or baseline detector 132.

Transmitted light 144 passes from the chopper wheel 118 into a collimating Fresnel lens 136, which in this example is sized to be about 1.5 square inches and is spaced about 0.6 inches from the chopper wheel 118. The transmitted light 144 passes through another adjustable aperture 112C in the bulkhead 112A and impinges upon a second mirror 124B, which directs the transmitted light 144 toward a sample W in a container C, such as a mixing vat or blender. The skilled artisan will recognize that the container could be a conveyor belt or other device for holding or transporting the sample and is not limited to an enclosed container.

As shown in FIG. 3, the transmitted light 144 is focused by the focusing Fresnel lens 126, which in this example may be round and about $15/16$ inches in diameter and is adjustable with an inner tube 122. Also in this example, lens 126 may be positioned about 0.6 inches from an outer surface of the container C. As shown, the transmitted light 144, now focused, passes through a transmissive window 113, which in this example is approximately 1 inch in diameter and which may include an anti-reflective (AR) coating disposed on one or both sides of window 113. The AR coating ensures that a chemical process in the container C does not interfere with the measuring process of the optical analysis system 110. Thus, the transmitted light 144 enters the container C and reflects from the sample as a carrier light 146. Lens 126 may also, or alternately, have an anti-reflective coating on one or both sides. By way of example only, the sample may be a moving mixture, such as aspirin and an excipient being blended in real time, or a plurality of tablets passing by on a conveyor belt at high speed.

FIG. 3 further illustrates that the carrier light 146 is directed by the tube 122 in a direction of the first detector 130. Eventually, the carrier light 146 impinges on the beam splitter 128 and a portion passes in a direction of the detector 132 for baselining with the portion 135B of the calibration light 135. This portion of the carrier light 146 is focused by lens 154 and received by the detector 156. Another portion of the carrier light 146 passes through MOE 148, which as noted above, has been selected for the chemical of interest based on the various components of the system 110. Finally, that portion of the carrier light 146, having passed through the MOE 148, is focused by lens 150 and received by the detector 152. As described above, the two signals collected by the detectors 130 and 132 may be manipulated, e.g., mathematically, to extract and ascertain information carried by the carrier light 146 about the sample W.

Figure 4A:
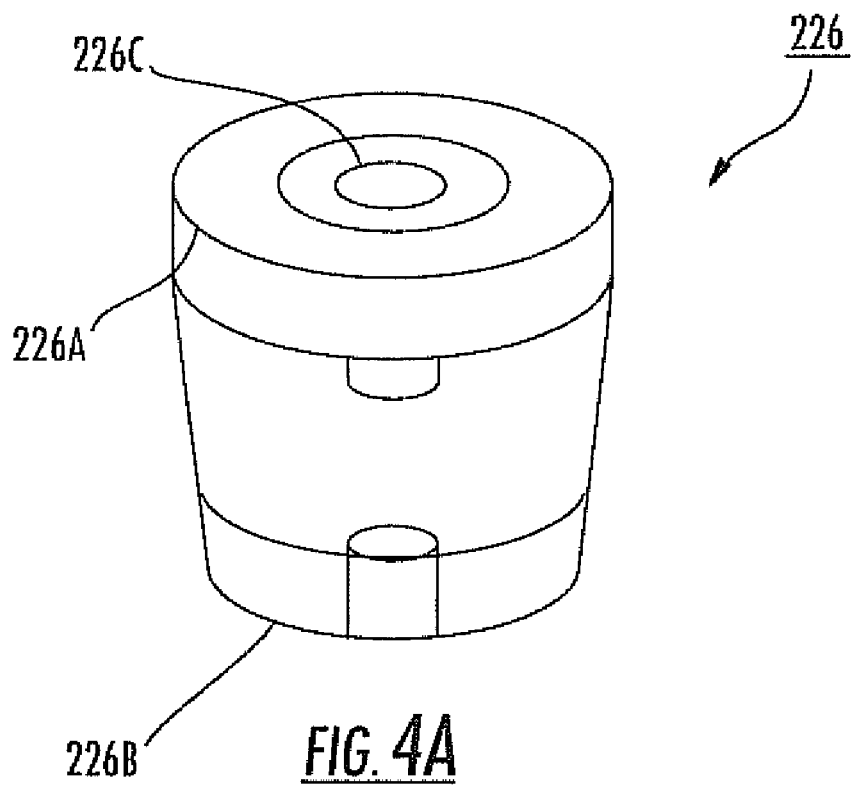
FIG. 4A is a perspective view of a retroreflecting mirror for use in the embodiments of FIGS. 1-3 according to a further aspect of the disclosure.
Figure 4B:
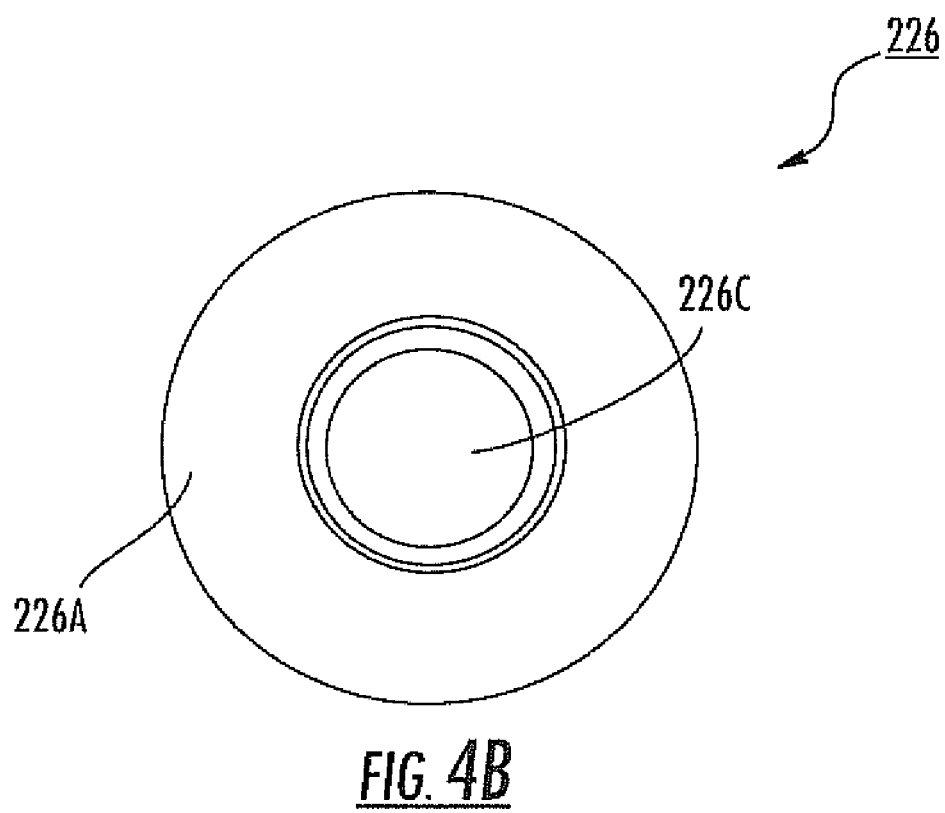
FIG. 4B is an end view of the retroreflecting mirror as in FIG. 4A.

Turning now to FIGS. 4A and 4B, detailed views of a retroreflector or collimating mirror 226 are shown. In this example, the mirror 226 has a first end 226A and a second end 226B and is generally cylindrically shaped. The mirror 226 is also coated with a reflective surface such as aluminum (Al), gold (Au), or other elements or materials dictated by the desired spectral region. The skilled artisan will appreciate that other shapes and reflective coatings may be provided to meet specific design requirements and characteristics of the target sample; thus, the mirror 226 is not limited to the exemplary embodiment shown in FIGS. 4A and 4B.

With reference to FIGS. 3, 4A, and 4B, the mirror 226 is useful for analyzing translucent liquids, for example, since liquids, in contrast to powders, do not readily create a diffuse reflectance to produce the desired carrier light 146 as shown in FIG. 3. By way of example operation, the lens 126 in FIG. 3 may be removed and replaced with the mirror 226 for retroreflection of the light 144 for transreflection measurement of the carrier light 146 for liquid sample analysis.

Figure 5:
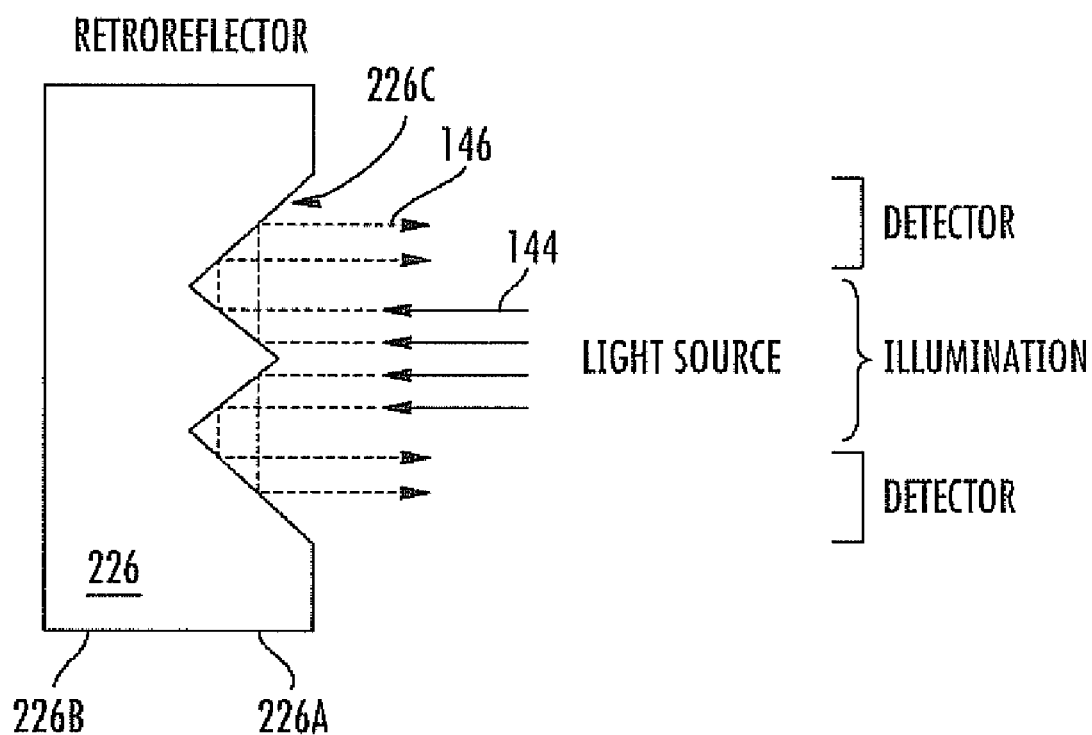
FIG. 5 is a cross section of the retroreflecting mirror taken along lines V-V in FIG. 4B.
Figure 6:
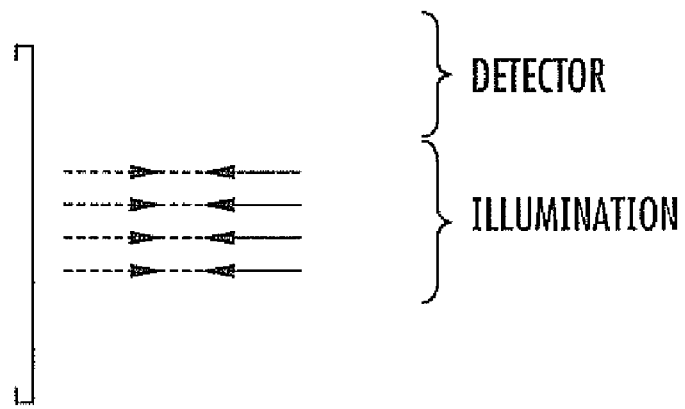
FIG. 6 is a partial, schematic view of a conventional mirror.

As shown in the cross section of FIG. 5, the light 144 passes through a first end 226A of mirror 226 and is collimated, as it exits the second end 226B of mirror 226 and enters into the liquid sample in the container (not shown). The carrier light 146 reflects from the liquid sample and returns through the first end 226A, which defines one or more conical shaped depressions or indentations 226C. The conical shaped indentations 226C direct the carrier light 146 in a manner similar to the example shown in FIG. 3 (that is, the carrier light 146 is diverted along a different path than the light 144). As a result, a portion of the carrier light 146 is directed through the MOE 148, as shown and described above. In contrast, a flat mirror as shown in FIG. 6 reflects a light ray back along a same ray path as an illumination source, such that any information carried by the reflected light ray would at least interfere with the illumination source but possibly be unreadable by a detector offset from illumination source.

With reference now to FIG. 7A, a third exemplary embodiment of the present subject matter, a wireless optical analysis and measurement system, is designated generally by reference number 310. Many aspects of the wireless optical analysis and measurement system 310 and its related components are similar to the foregoing embodiments; thus, for the sake of brevity, these components and their function are merely summarized below. To provide a full and enabling disclosure of the optical analysis system 310, however, when like or similar elements and components are not specifically described below, implicit reference is made to the foregoing descriptions.

Figure 7B:
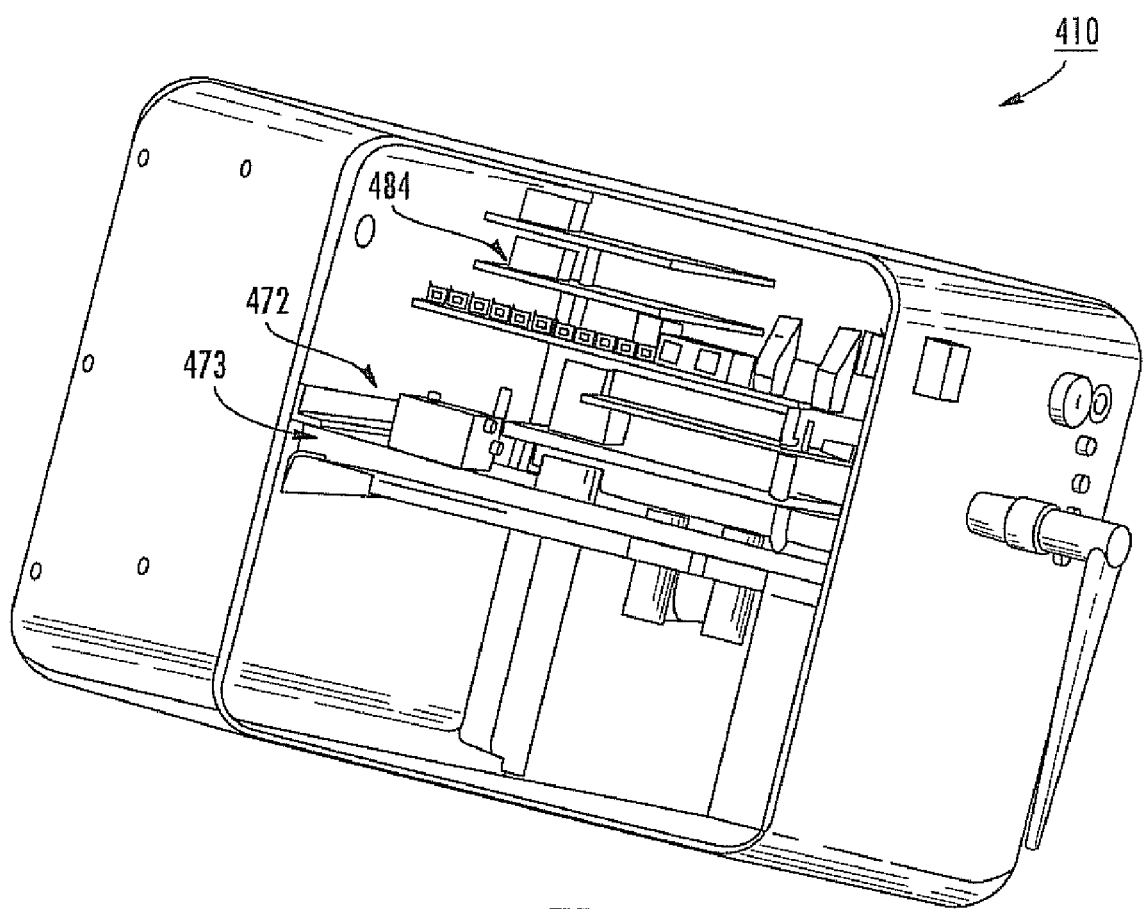
FIG. 7B is a perspective view of a wireless unit similar to FIG. 7A in accordance with a further aspect of the present disclosure.
Figure 8:
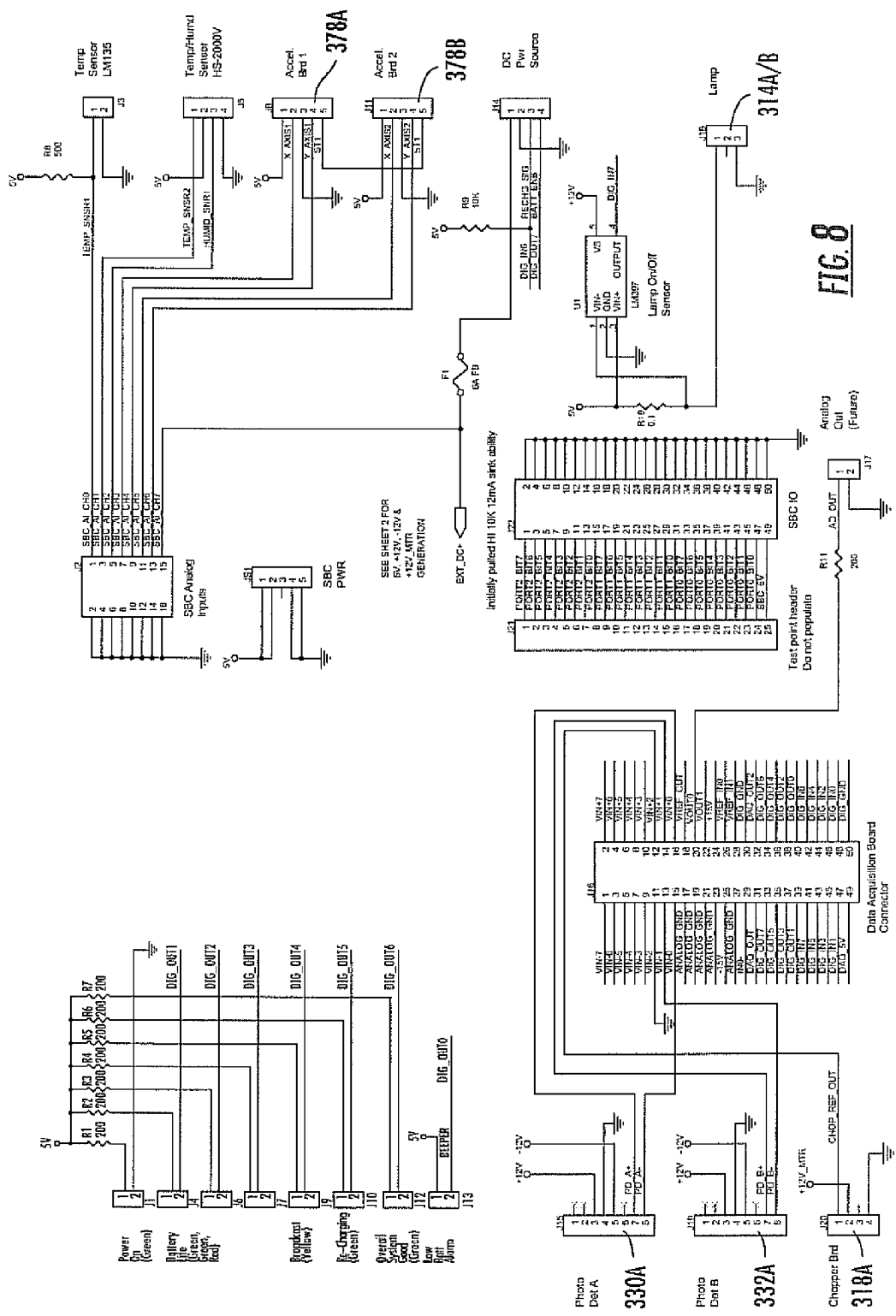
FIG. 8 is schematic diagram of the wireless unit as in FIG. 7A.
Figure 9:
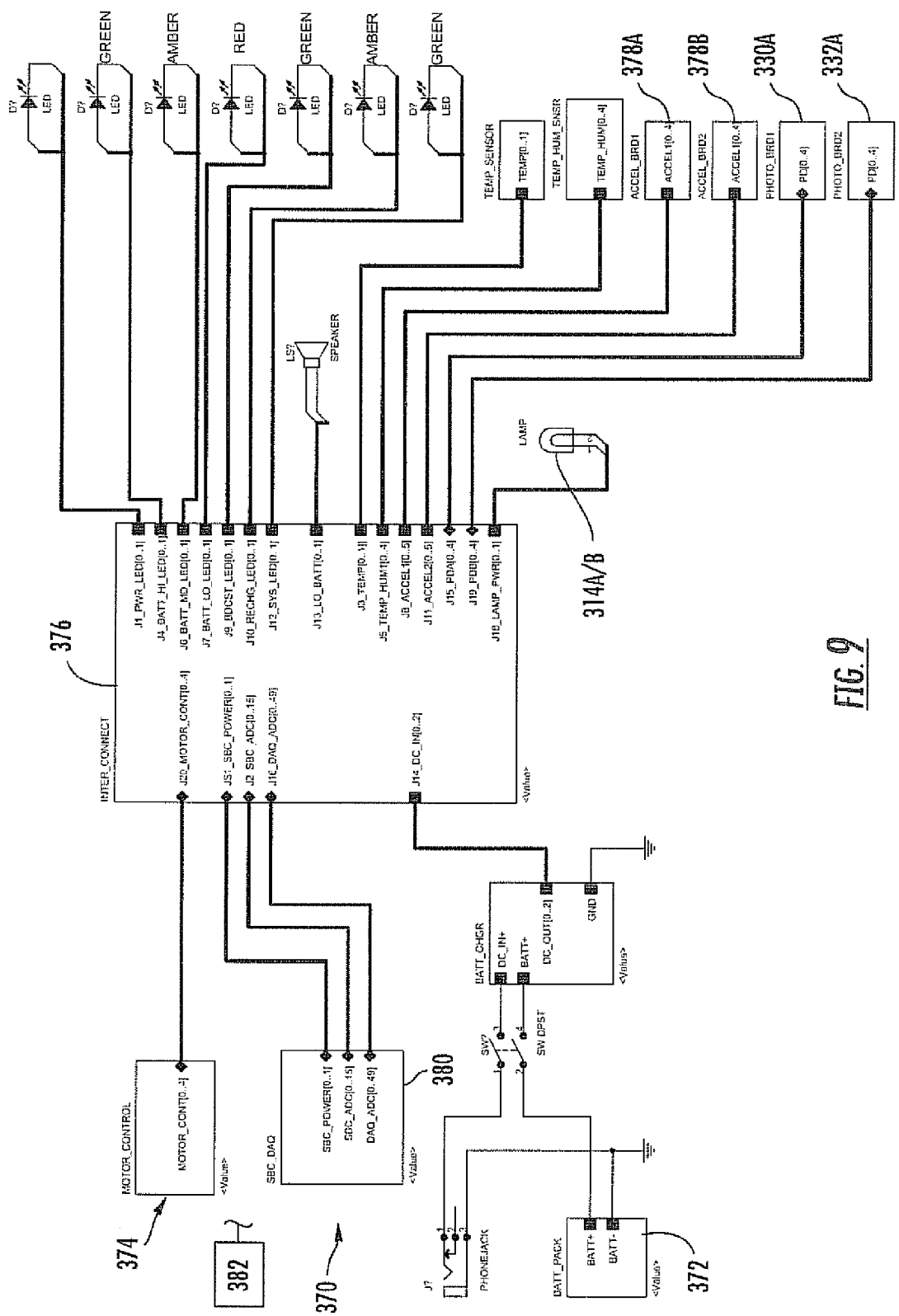
FIG. 9 is a schematic diagram of an interconnect board circuit of the wireless unit as in FIG. 7A.

As shown in FIGS. 7A, 8, and 9, the wireless optical analysis system 310 incorporates an optical computing system substantially as described above. More specifically, the wireless system 310 includes a housing 312, illumination or light sources 314A, 3148, a chopper wheel 318, one or more spectral elements 320, a focusing lens 326, a beam splitter 328, a first detector 330 including a multivariate optical element 348, and a second detector 332.

Briefly restated with reference to FIG. 7A, illumination sources 314A, 314B generate a source light 334, which is focused through respective lenses 316A, 3168 located proximate to the illumination sources 314A, 314B. The source light 334 then travels past a beam splitter 336 and is focused through a chopper-focusing lens 317. Source light 334 next passes through windows 338 in a chopper wheel 318, such windows 338 being defined as transmissive areas between spokes 340.

After passing through the chopper wheel 318, whose rotation produces a modulated light beam, source light 334 then passes through one or more spectral elements 320 and reflects off a turning mirror 324. Turning mirror 324 causes the reflected light 344 to be directed through the inner annular region 342A of a concentric sampling tube 322. Reflected light 344 travels through a Swagelok®-type connector 362 having, at its distal end, a focusing lens 366, and to the end of tube 322, where reflected light 344 passes through focusing lens 326 and through a transmissive window 313 in container C.

Container C, as before, holds sample material W. Within container C, reflected light 344 interacts with material of interest W and is reflected back from material W as data-carrying, or carrier, light 346 through outer annular region 342B of tube 322.

Returning to the optical analysis device 310, carrier light 346 reaches beam splitter 328, which divides the light. Some of the carrier light 346 is sent in the direction of a detector 330 with a multivariate optical element (MOE) 348, through lens 350, and onto photodetector 352. This portion of the light may be referred to as "Signal A." The other portion of the carrier light 346 is sent through lens 354 and onto photodetector 356 on a detector 332. This second portion of the light may be referred to as "Signal B," which acts as a reference signal.

The detectors 330, 332 communicate with a gain mechanism 364, which compares the light of "Signal A" with that of "Signal B" and relays this information as a mathematical expression (e.g., a ratio) to system 368. System 368 continuously averages the instantaneous measurements (that is, the ratios of Signal A to Signal B) for analysis and monitoring to provide continuous, real-time reporting of product and/or process conditions.

As its name implies, the wireless system 310 shown in FIGS. 7A, 8, and 9 is designed for remote operation. As shown, the wireless system 310 incorporates a signal and data processing computer 370, a rechargeable battery 372, and wireless control and communication 374 capabilities into a single unit. The wireless system 310 can be operated temporarily in a fully wireless mode using the included rechargeable battery 372, or in a powered mode for continuous operation. When operating in the powered mode, the battery 372 serves as an uninterruptible power supply. By way of example, the wireless system 310 can operate for 6 or more hours on the battery 372 between recharging.

As further shown in FIGS. 7A and 9, the battery 372 is connected to an interconnect board 376 with a relatively lower voltage threshold, which enables a greater range of usable voltage from the battery 372. Also shown, an orientation check-accelerometer 378 (and associated boards 378A, 378B, shown in FIGS. 8 and 9) makes the wireless system 310 ideal in moving applications, such as for use with a pharmaceutical mixer C. In such a moving mixer C, material W is being tumbled inside the moving vessel C. As such, the material W being measured is not always in contact with a measurement window (see, e.g., window 113 in FIG. 3). In such cases, the wireless system 310 is designed to measure the material W only when the material W is in contact with the measurement window. Therefore, the accelerometer 378 serves to communicate position information to the computer 370 (shown in FIGS. 7A and 9) such that only system output from the period when the material W is in contact with the measurement window is used for concentration measurements.

Figure 7C:
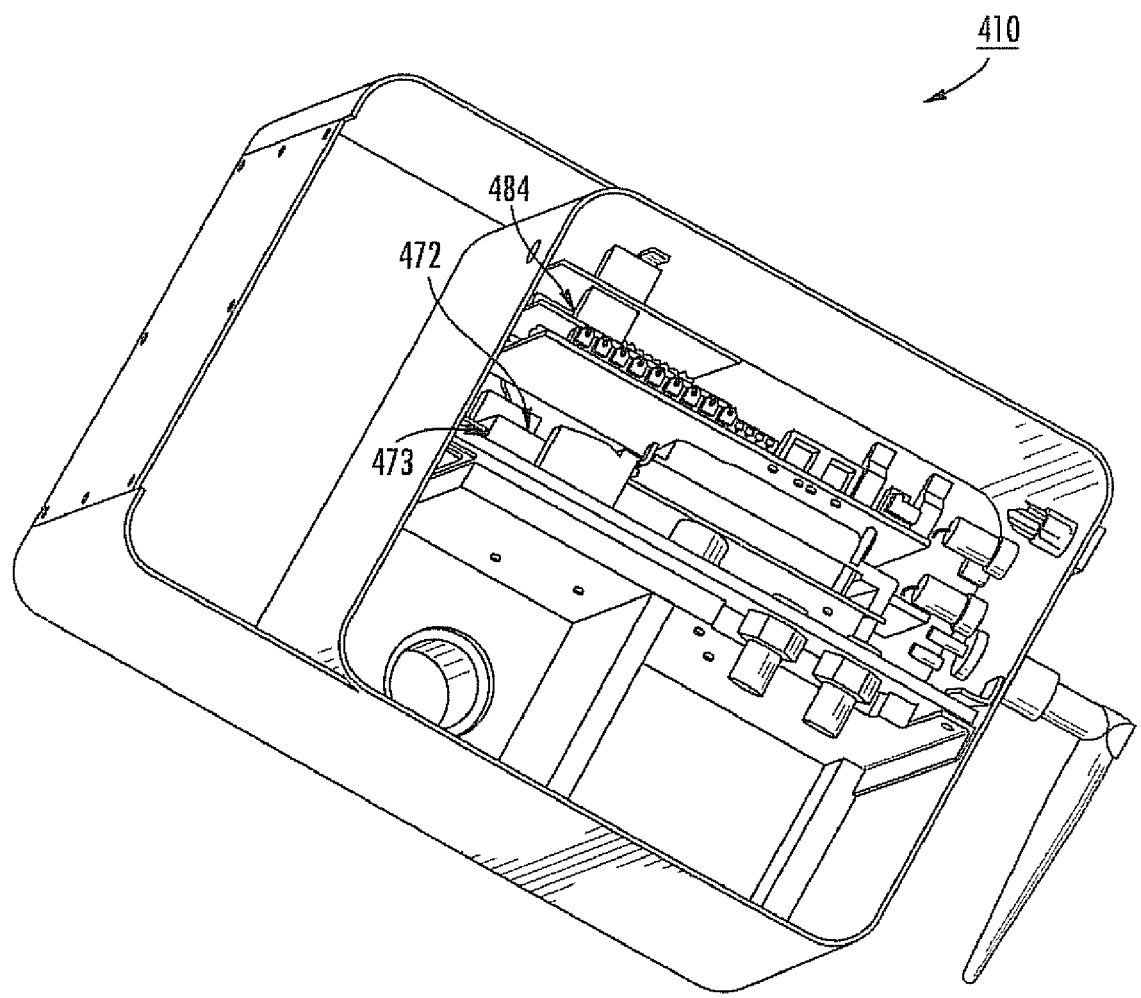
FIG. 7C is another perspective view of the wireless unit in FIG. 7B.

FIGS. 7B and 7C show another exemplary embodiment of the present subject matter, a wireless optical analysis and measurement system, which is designated generally by reference number 410. As shown, the wireless optical analysis and measurement system 410 includes a battery 472 with a battery recharge board 473, an A/D converter 484, and an optical computer. Many aspects of the wireless optical analysis and measurement system 410 and its related components are similar to the foregoing embodiments. Therefore, reference is made to the foregoing descriptions to provide a full and enabling disclosure of the optical analysis system 410.

FIG. 8 shows a control board 314A/B associated with illumination sources 314A, 314B. Further, as described above, the control boards 378A, 378B associated with the operation of the accelerometer are also provided. Control boards 330A, 332A operate detectors 330, 332, respectively, while the chopper wheel 318 is controlled by control board 318A.

FIG. 9 most clearly shows that the on-board computer 370 includes a data acquisition and conversion (DAQ) card 380 (shown in phantom line in FIG. 7A). The on-board computer 370 is capable of signal processing and includes appropriate software loaded for a desired analyte analysis. As shown schematically, a central computer system 382 (also shown in FIG. 7A) may be used to monitor and control several measurement systems, including the wireless system 310. As known to those skilled in the art, the wireless system 310 may be programmed or controlled to send data to the central computer system 382 to provide data back-up. Also shown in FIG. 9 are control boards 330A, 332A for detectors 330, 332; control boards 378A, 378B for accelerometer 378; battery 372; illumination sources 314A, 314B; and motor control 374 for wireless control and communication.

Figure 10:
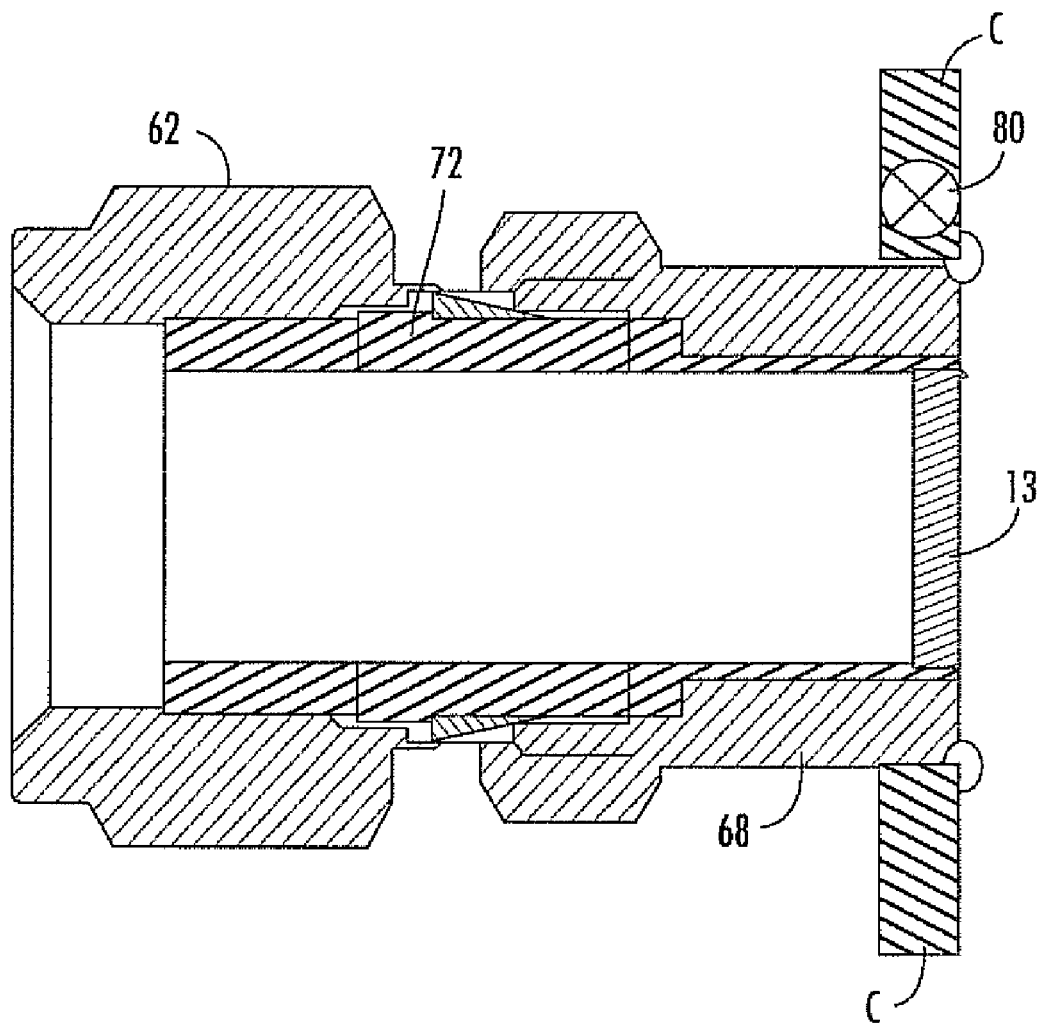
FIG. 10 is a partial cross section taken proximate element 66 in FIG. 1.

With reference to FIGS. 1 and 10, by connecting the housing 12 of the optical analysis or measurement system 10 directly to a process line (see also FIGS. 11, 12 and 13), no fiber optic probe or other device is needed to connect the system 10 and the process line. This direct connection permits the system 10 to be designed to operate over a wider spectral region, which expands the potential applications where useful measurements can be made.

As shown in FIG. 10, for instance, the union is accomplished using a shoulder fitting assembly 72 for reproducible installation to ensure the same or similar systems 10 mate at a uniform distance from the interrogation window 13, e.g., about ⅛ inch in this example. This arrangement enables a more reproducible installation. The interrogation window 13 may be made of sapphire. The fitting assembly may be a Swagelok® type connector having a first connector 62 extending from the optical analysis system and a mating connector 68 extending from the wall of container C. Additionally, any of several other methods may be used to connect the system 10 and the process line including using a sanitary fitting connection, such as male or female quick disconnect fitting and the like.

As further shown in FIG. 10, the interrogation window 13, positioned in the wall of container C, may include a window clearing system 80 to clear the target material from interrogation window 13. Such a window clearing system 80 may be in the form of a wiper system or an air (or other gas) purge.

Figure 11:
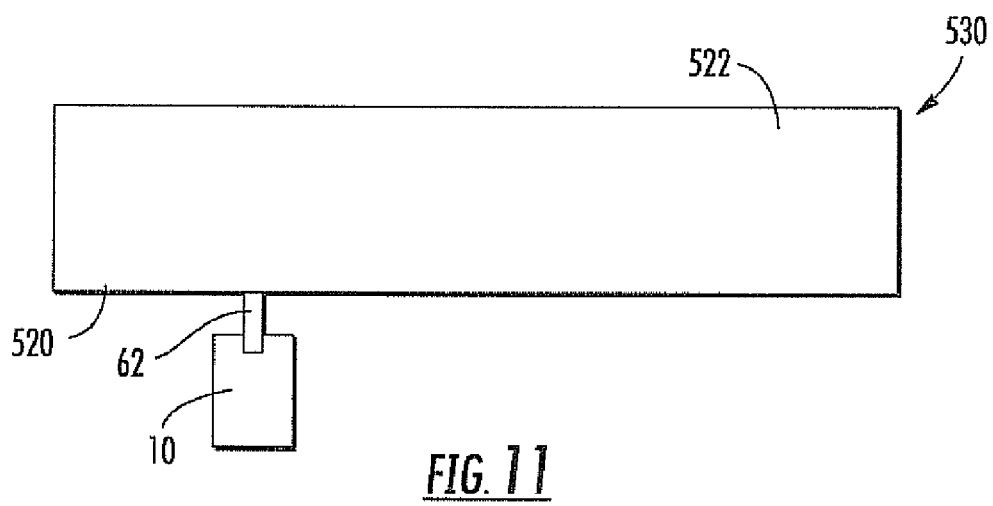
FIGS. 11, 12 and 13 are schematic views of real time measurement systems being used in exemplary manners according to further aspects of the present disclosure.
Figure 12:
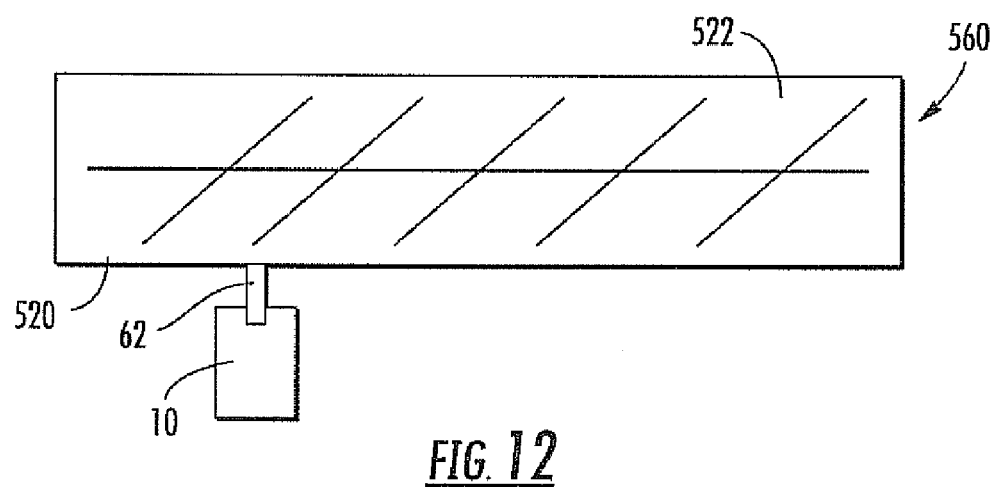
Figure 13:
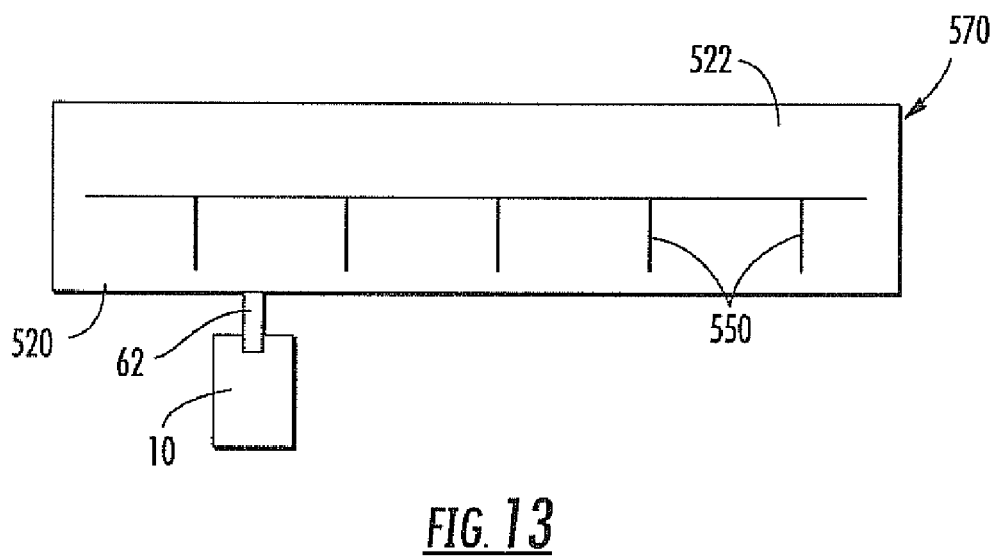

FIGS. 11, 12 and 13 show real-time measurement systems that enable a user to collect instantaneous data about various process streams. As shown, the real-time measurement systems average signal output over a predetermined time period to improve the signal-to-noise ratio of measurements of product in the process streams.

For example, as shown most clearly in FIG. 11, a measurement system 10, as described above, is installed at a measurement point on a wall 520 of a transport conveyor 530. This exemplary measurement system provides a reflectance measurement on material moving along the transport conveyor belt 522; i.e., the process stream. The measurements are provided in the form of a mathematical relationship (e.g., a ratio) of light signals A and B, as described previously. Because Signal A and Signal B are produced by modulated light beams, the measurements are similarly generated on a frequency corresponding to the modulation frequency. A number of these instantaneous measurement results (i.e., the ratios of Signal A to Signal B) may be averaged over a desired time period to provide a continuous rolling average of conditions within the product and/or process. The time series for producing such rolling averages may be, for example, from about less than 0.1 seconds to several minutes to more than 30 minutes, depending on the demands of the particular application. This mode of continuous (or rolling) averaging enables development of a calibration for several different products using the same optical computing system.

A variation of the embodiment in FIG. 11 is to monitor a mixing process in a blender (not shown) or to monitor a conversion of a chemical reaction in a process vessel (not shown). Depending on the material being monitored and the configuration of the sampling point, this could be a reflectance measurement, a transflectance measurement, or a transmission measurement. In this scenario, measurements may be taken to indicate the presence, or amount, of a reaction product (or by-product), which may be used as an indicator of when a reaction should properly be stopped. For example, the presence of a desired amount of a reaction product—as indicated by the continuous rolling average provided by the optical analysis system—may be communicated to the control systems for the process vessel, thereby providing an indicator of when the reaction should be stopped.

Additional examples include a sampling lens and associated optics, which may be a focusing lens on a point, or a transmission or transflectance system which enables monitoring through a moving cylindrical sample. Such a sample could be a flowing process stream, or material exiting an extruder die, or the like.

FIG. 12 illustrates a measurement system, engaged with a screw-type conveyor 560, via connector 62. In this instance, the measurements are made through an interrogation window (not shown) in the wall 520 of the conveyor 560. The target material is pushed over conveyor bed 522 by a screw 540, which carries the target material past the interrogation window, where it is measured using the optical analysis system 10.

FIG. 13 illustrates another variation of the conveyor systems of FIGS. 11 and 12. In this system, a paddle conveyor 570, having a conveyor bed 522 and conveyor paddles 550, is used to move the target material past an interrogation window (not shown) in the wall 520 of paddle conveyor 570. Again, as before, an optical analysis system 10 is positioned proximate to the conveyor wall by connector 62.

By averaging over time as introduced above, potentially interfering effects of a moving screw drive (e.g., FIG. 12), conveying paddles (e.g., FIG. 13), or the like do not interfere with the system measurement result. More particularly, by adjusting the slope and offset of the calibration, valid measurements on a range of different products using the same MOE of different materials, across a broad range of interferents, are possible. In addition, this enables the measurement of specific analyte of interest, such as moisture or fat or protein or the like, across a wide range of different products. An example is a system designed to measure the moisture content in pet food. More particularly, the MOE may be designed to measure fat and is not dependent on product or protein or other characteristics of the product. As above, the system outputs may be communicated using wired or wireless technologies.

Of further benefit, the optical analysis systems, as described herein, may be configured to communicate with process control equipment, such that process modifications may be made in real-time in response to trends or anomalies in measurement results. For example, if the optical analysis system is configured to measure moisture content in pet food and the rolling average of moisture content over some period of time trends steadily upward, then the optical analysis system may convey an instruction to process control equipment to increase drying time or drying temperature to correct this deviation.

In several instances, the multivariate optical computing systems as described above may be used to measure different materials including differently shaped materials and differently sized materials; e.g., cylindrical shaped pieces, or other shapes, and/or disparate shapes. By adjusting the averaging time based on the needed process response, calibrations are developed for these different materials. Furthermore, materials with different colors (including red, green, orange, brown, and tan) have been measured using the optical computing system. Making the measurement in the NIR spectral region reduces the difference between these colored samples because the product colors are less distinct in that spectral range; i.e., colorants are not as active in this region.

As further shown in FIGS. 11, 12 and 13, by installing measurement points and interrogation windows on the bottoms of transport conveyors, the material passing over the windows provides self-cleaning at the measurement points. Additionally, or in the alternative, the window may use a wiper system or air or other gas purge being used to clear the window as shown in FIG. 10.

The skilled artisan will appreciate that the disclosure is not limited to the foregoing exemplary arrangements. For example, the systems can be arranged with the mirrors and the detectors on an opposite side of the container C such that the light passes through the liquid sample into the mirror. Accordingly, in this alternatively arranged system, particle density in a fluid can be studied in conjunction with a chemical content of the fluid.

The disclosure may be better understood from the following tests and examples.

EXAMPLE I

System I

A system similar to the optical analysis system 10 shown in the figures was constructed and used to make static measurements on aspirin/lactose.

System I Components:
Illumination: 20 W Gilway lamp
Spectral elements: 5 mm D2O, 5 mm Germanium
Optical window: none
Detector: PbS detector from New England Photoconductor
MOE: specific to test conditions.

Procedure and Results of Static Testing Using System I:

A powdered sample with a known composition was placed in a dish and the system light beam was focused on the powder. The output of the detectors was monitored and recorded. Aspirin/lactose samples covering the range of 100% aspirin to 100% lactose were tested.

EXAMPLE II

System II

A system similar to the optical analysis system 10 shown in the figures was constructed and used to make dynamic measurements on aspirin/lactose.

System II Components:
Illumination: 20 W Gilway lamp
Spectral elements: 5 mm D2O, 5 mm Germanium
Optical window: sapphire window
Detector: PbS detector from New England Photoconductor
MOE: specific to test conditions.

Procedure and Results of Dynamic Testing Using System II:

The Aspirin/Lactose testing was made on a mixer bowl containing lactose and the system measured as aspirin was added to the system and mixed. Specifically, lactose powder was placed in the bowl of a mixer and the measurement system was attached the bowl using a Swagelok® brand fitting. A sapphire window was used to contain the powder in the bowl and allow the system to interrogate the powder. With the mixer turning, known amounts of aspirin were added and the system output signal was monitored and recorded. Aspirin was added in several allotments to about 37% final aspirin concentration.

EXAMPLE III

System III

A system similar to the optical analysis system 10 shown in the figures was constructed and used to make static measurements on aspirin/lactose.

System III Components:
Illumination: 5 W Gilway lamp
Spectral elements: 5 mm D2O, 5 mm Germanium
Optical window: none
Detector: PbS detector from New England Photoconductor
MOE: specific to test conditions.

Procedure and Results of Dynamic Testing Using System III:

Similar to the examples above.

EXAMPLE IV

System IV

A system similar to the optical analysis system 10 shown in the figures was constructed and used to make dynamic measurements on dog food samples.

System IV Components:
Illumination: 5 W Gilway lamp
Spectral elements: specific to test conditions.
Optical window: sapphire
Detector: PbS detector from New England Photoconductor
MOE: specific to test conditions.

Procedure and Results of Dynamic Testing Using System IV:

Commercial dog food samples were taken and the moisture content was modified by drying some samples and adding moisture to others. These various samples were tested in a flowing condition to demonstrate the applicability of continuous averaging as described hereinabove.

Although examples have been described in such a way as to provide an enabling disclosure for one skilled in the art to make and use the disclosure, it should be understood that the descriptive examples of the disclosure are not intended to limit the disclosure to use only as shown in the figures. For instance, the housing 12 may be shaped as a square, an oval, or in a variety of other shapes. Further, any of a variety of light sources may be substituted for those described above. The disclosure is intended to claim all such changes and modifications as fall within the scope of the appended claims and their equivalents. Thus, while exemplary embodiments of the disclosure have been shown and described, those skilled in the art will recognize that changes and modifications may be made to the foregoing examples without departing from the scope and spirit of the disclosure.

That which is claimed is:

1. A method of using multivariate optical computing to collect real-time data about a process stream of a target material, said method comprising:
    installing an optical analysis system proximate a process line, the process line having a transmissive window installed therein and being configured to move the target material past the transmissive window for analysis by the optical analysis system;
    using an optical element in the optical analysis system to form a first aperture and a second aperture, the optical element excluding light passing through the first aperture from passing through the second aperture;

illuminating a portion of the target material in the area of the transmissive window with a modulated light from the optical analysis system through the first aperture;

capturing a reflected light from the illuminated portion of the target material through the second aperture;

directing a portion of said reflected light through at least one multivariate optical element in the optical analysis system to produce a stream of instantaneous measurement results; and continuously averaging the stream of instantaneous measurement results over a period of time to determine an overall measurement of said property of the target material.

2. The method of claim 1, wherein the optical analysis system operates in one of reflectance mode and transmission mode.

3. The method of claim 2, wherein the optical analysis system operates in reflectance mode.

4. The method of claim 1, wherein the optical analysis system is connected directly to the process line via a fitted connector, the fitted connector being aligned with the transmissive window.

5. The method of claim 1, wherein the process line comprises a container selected from the group consisting of a mixing vat, a reaction vessel, a blender, a transport conveyor, a screw conveyor, and a paddle conveyor.

6. The method of claim 1, wherein said light is infrared light.

7. The method of claim 1, wherein a second portion of said reflected light is directed to a second photo-detector in the optical analysis system to produce a second stream of instantaneous measurement results.

8. The method of claim 7, wherein said second stream of instantaneous measurement results is averaged and compared to said first stream of instantaneous measurement results.

9. The method of claim 1, wherein said period of time is up to about 60 minutes.

10. The method of claim 1, further comprising providing a window clearing system proximate to the transmissive window, the window clearing system being configured to clear the target material from the transmissive window.

11. The method of claim 10, wherein the window clearing system comprises one of a wiper system and an air purge system.

12. An optical analysis system for continuous collection of real-time data about at least one chosen property of a target material, the target material being part of a process stream, the process stream including a container having an interrogation window therein, whereby said optical analysis system interacts with the target material via the interrogation window, said optical analysis system comprising:

a light source being configured to radiate a source light;

a modulator disposed in a path of said source light, the modulator being configured to modulate said source light into light pulses at a desired frequency;

an optical element in the optical analysis system to form a first aperture and a second aperture, the optical element excluding light passing through the first aperture from passing through the second aperture;

a spectral element disposed proximate the modulator, the spectral element being configured to filter the source light pulses passing through the first aperture for a spectral range of interest of the target material;

a beamsplitter configured to split the source light pulses passing through the second aperture, once said source light pulses have been reflected by the target material, into a first portion of reflected light pulses and a second portion of reflected light pulses;

an optical filter mechanism disposed to receive the first portion of reflected light pulses, the optical filter mechanism being configured to optically filter data carried by the first portion of reflected light pulses into at least one orthogonal component;

a first detector mechanism in communication with the optical filter mechanism to measure the orthogonal component of the data carried by the first portion of reflected light pulses;

a second detector mechanism being configured to receive a second portion of reflected light pulses and to measure the property of the data carried by the second portion of reflected light pulses; and a computer configured to continuously generate a ratio of the orthogonal component of the data carried by the first portion of reflected light pulses and the data carried by the second portion of reflected light pulses and to continuously average, over a period of time, the generated ratios to provide a rolling average of the chosen property of the target material.

13. The optical analysis system of claim 12, wherein the optical analysis system further comprises a window cleaning system, said window cleaning system being located within the container proximate to the interrogation window.

14. A method of using multivariate optical computing in real-time or at high speed for determining information about a sample from light interacting with the sample by averaging an instantaneous measurement result of the sample, the method comprising:

using an optical element for modulating the light interacting with the sample at a desired frequency; and using an optical element to form a first aperture for passing a light illuminating the sample and a second aperture for passing a light reflected by the sample, the optical element excluding the illuminating light from passing through the second aperture.

15. The optical analysis system of claim 12 further including an accelerometer to ensure that data is collected only while the optical analysis system is in a proper orientation.

16. The method of claim 14, further comprising providing a selected amount of calibration light to calibrate the information about the sample.

17. A method of using multivariate optical computing to collect real-time data about a process stream of a target material, said method comprising:

installing an optical analysis system proximate a process line, the process line having a transmissive window installed therein and being configured to move the target material past the transmissive window for analysis by the optical analysis system;

illuminating a portion of the target material in the area of the transmissive window with a modulated light from a source in the optical analysis system, said light being in the form of light pulses;

capturing said light pulses as said pulses are reflected from the illuminated portion of the target material, said pulses carrying information about a property of the illuminated portion of the target material;

directing a portion of said information-carrying pulses through at least one multivariate optical element in the optical analysis system to produce a stream of instantaneous measurement results;

continuously averaging the stream of instantaneous measurement results over a period of time to determine an overall measurement of said property of the target material;

forming a calibration light from the illuminating modulated light from the source in the optical system; and directing the calibration light through the at least one multivariate optical element to calibrate the overall measurement.

18. The method of claim 1, wherein the target material comprises a combination of solids and fluids including a petroleum product.

19. The optical analysis system of claim 12, wherein the target material comprises a combination of solids and fluids including a petroleum product.

20. The method of claim 1, wherein the multivariate optical element produces light having the same principal components of gasoline.

21. The optical analysis system of claim 12, wherein the period of time is up to 60 minutes.

22. The optical analysis system of claim 12, wherein the chosen property is selected from the group consisting of a reaction product content, a nutrient content, a moisture content, a fat content, a protein content, a carbohydrate content, a pharmaceutical characteristic, an alcohol content, a cholesterol content, and combinations thereof.

23. An optical analysis system for continuous collection of real-time data about at least one chosen property of a target material, the target material being part of a process stream, the process stream including a container having an interrogation window therein, whereby said optical analysis system interacts with the target material via the interrogation window, said optical analysis system comprising:

a light source configured to radiate a source light;

a modulator disposed in a path of said source light, the modulator being configured to modulate said source light into light pulses at a desired frequency;

a spectral element disposed proximate the modulator, the spectral element being configured to filter said source light pulses for a spectral range of interest of the target material;

a beamsplitter configured to split said source light pulses, once said source light pulses have been reflected by the target material, into a first portion of reflected light pulses and a second portion of reflected light pulses;

an optical filter mechanism disposed to receive the first portion of reflected light pulses, the optical filter mechanism being configured to optically filter data carried by the first portion of reflected light pulses into at least one orthogonal component;

a first detector mechanism in communication with the optical filter mechanism to measure the orthogonal component of the data carried by the first portion of reflected light pulses;

a second detector mechanism being configured to receive a second portion of reflected light pulses and to measure the property of the data carried by the second portion of reflected light pulses;

a computer configured to continuously generate a ratio of the orthogonal component of the data carried by the first portion of reflected light pulses and the data carried by the second portion of reflected light pulses and to continuously average, over a period of time, the generated ratios to provide a rolling average of the chosen property of the target material; and an optical element to direct a calibration light from the light source through the optical filter mechanism to calibrate the measurement of the property of the data carried by the second portion of reflected light pulses.

* * * * *